(12) United States Patent
Maekawa et al.

(10) Patent No.: US 10,648,825 B2
(45) Date of Patent: May 12, 2020

(54) PULSE WAVE MEASURING APPARATUS, CONTROL METHOD, AND NON-TRANSITORY COMPUTER-READABLE RECORDING MEDIUM

(71) Applicant: Panasonic Intellectual Property Management Co., Ltd., Osaka (JP)

(72) Inventors: Hidetsugu Maekawa, Nara (JP); Kenta Murakami, Osaka (JP); Mototaka Yoshioka, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 356 days.

(21) Appl. No.: 15/849,810

(22) Filed: Dec. 21, 2017

(65) Prior Publication Data

US 2018/0202823 A1 Jul. 19, 2018

(30) Foreign Application Priority Data

Jan. 19, 2017 (JP) .................................. 2017-007832

(51) Int. Cl.
*G01C 21/00* (2006.01)
*G01C 21/34* (2006.01)
(Continued)

(52) U.S. Cl.
CPC ..... *G01C 21/3453* (2013.01); *G01C 21/3461* (2013.01); *G01C 21/3602* (2013.01);
(Continued)

(58) Field of Classification Search
CPC ............ G01C 21/3453; G01C 21/3461; G01C 21/3697; G01C 21/3602; G06K 9/4652;
(Continued)

(56) References Cited

U.S. PATENT DOCUMENTS 8,725,311 B1 * 5/2014 Breed .................... A61B 5/163
701/1
2014/0276090 A1 * 9/2014 Breed ...................... A61B 5/18
600/473

(Continued)

FOREIGN PATENT DOCUMENTS

| JP | 8-159800 | 6/1996 |
| JP | 11-064976 | 3/1999 |

(Continued)

*Primary Examiner* — Ian Jen
(74) *Attorney, Agent, or Firm* — Wenderoth, Lind & Ponack, L.L.P.

(57) ABSTRACT

A pulse wave measuring apparatus includes a light emitter that illuminates with light having an amount an area containing a part of skin of a user staying in a vehicle, an imager that captures an image of the area, a controller that obtains a driving route from a departure point of the vehicle to a destination point of the vehicle, obtains an estimated time at which the vehicle passes through a location along the driving route, predicts an incident amount of sun light that enters the vehicle at the location at the estimated time, and calculates the amount under a condition that a sum of the predicted incident amount and the amount is a constant value, and a pulse wave calculator that calculates a pulse wave of the user using the image, and outputs pulse wave information of the user.

9 Claims, 19 Drawing Sheets

(51) Int. Cl.
- *G01C 21/36* (2006.01)
- *G06K 9/00* (2006.01)
- *G06K 9/46* (2006.01)
- *A61B 5/024* (2006.01)

(52) U.S. Cl.
CPC ..... *G01C 21/3697* (2013.01); *G06K 9/00221* (2013.01); *G06K 9/00255* (2013.01); *G06K 9/00845* (2013.01); *G06K 9/00885* (2013.01); *G06K 9/4652* (2013.01); *A61B 5/02427* (2013.01); *A61B 5/02433* (2013.01); *G06K 9/00375* (2013.01); *G06K 2009/00939* (2013.01)

(58) Field of Classification Search
CPC ........... G06K 9/00221; G06K 9/00845; G06K 9/00255; G06K 9/00885; G06K 9/00375; G06K 2009/00939; A61B 5/02427; A61B 5/02433; A61B 5/02; A61B 5/6893
See application file for complete search history.

(56) References Cited

U.S. PATENT DOCUMENTS

| | | |
|---|---|---|
| 2014/0303885 A1 | 10/2014 | Kamada et al. |
| 2017/0156673 A1* | 6/2017 | Uchida ................ A61B 5/6893 |
| 2018/0116604 A1* | 5/2018 | Newberry ............. G16H 40/63 |
| 2018/0202823 A1* | 7/2018 | Maekawa .......... G01C 21/3453 |

FOREIGN PATENT DOCUMENTS

| | | |
|---|---|---|
| JP | 2000-353295 | 12/2000 |
| JP | 2007-315799 | 12/2007 |
| JP | 2008-089570 | 4/2008 |
| JP | 2011-147469 | 8/2011 |

* cited by examiner

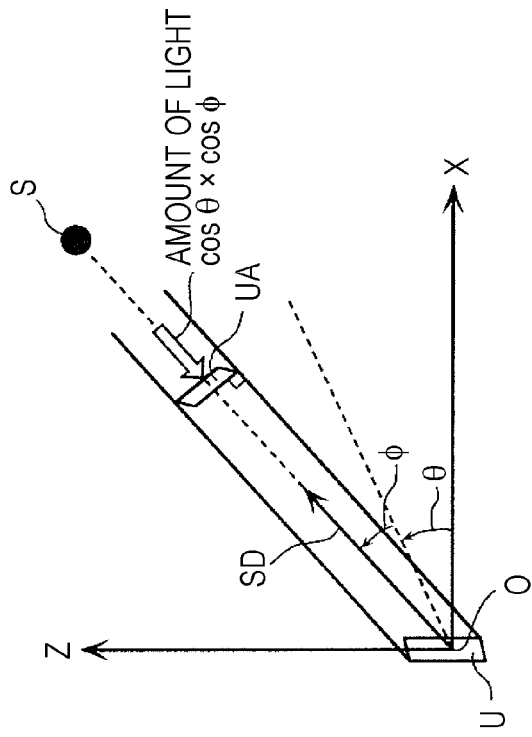
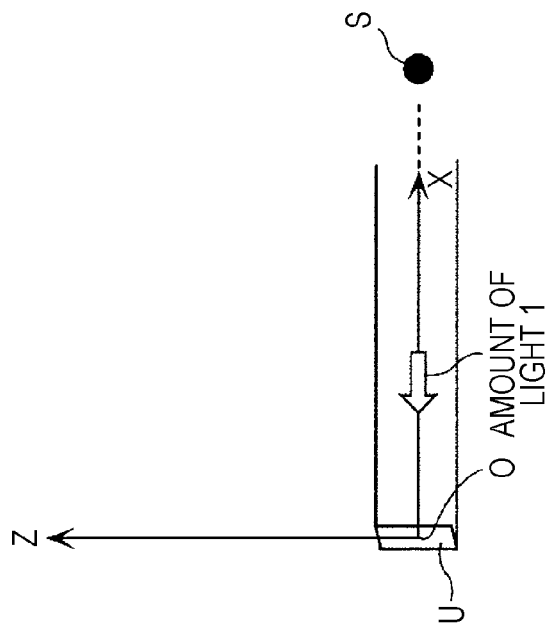

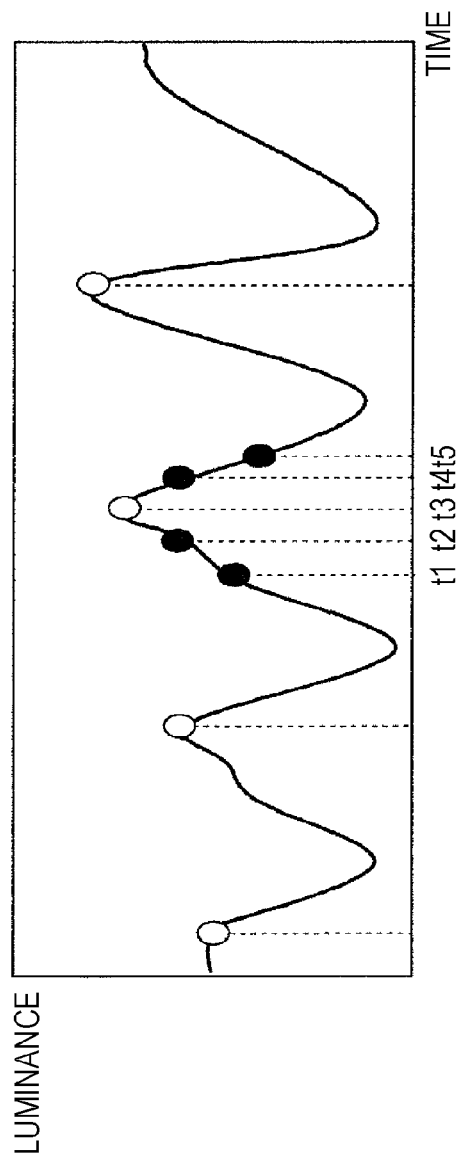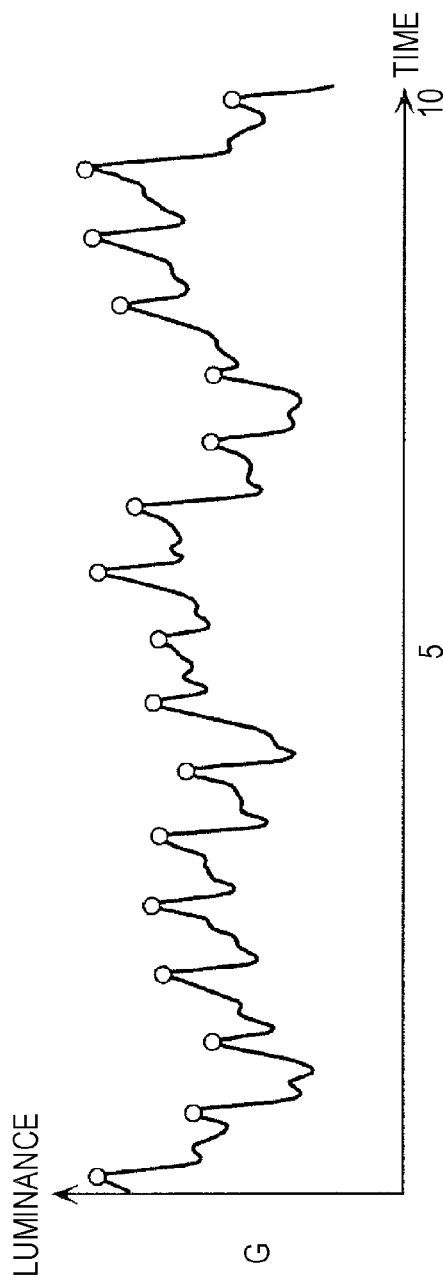

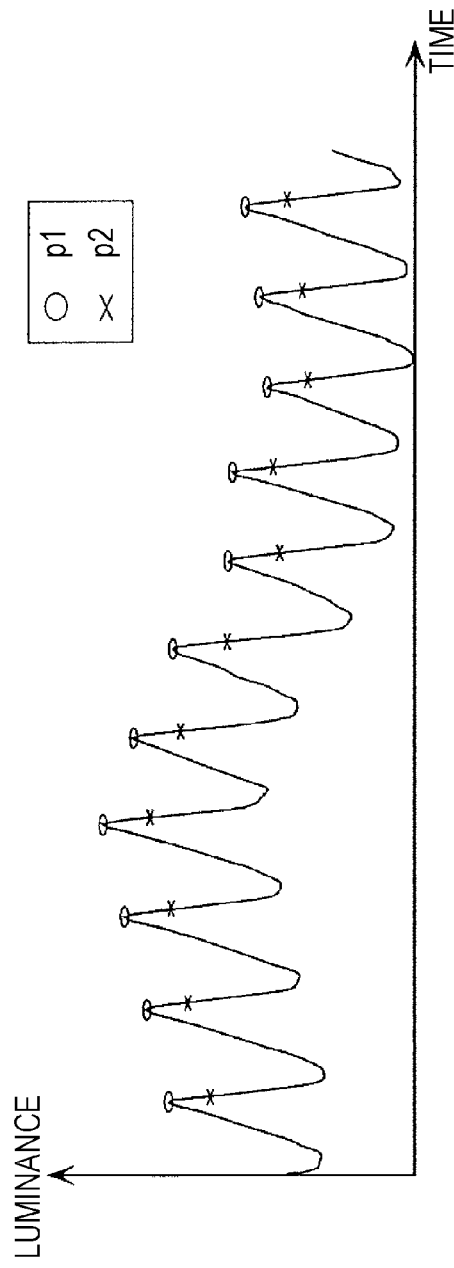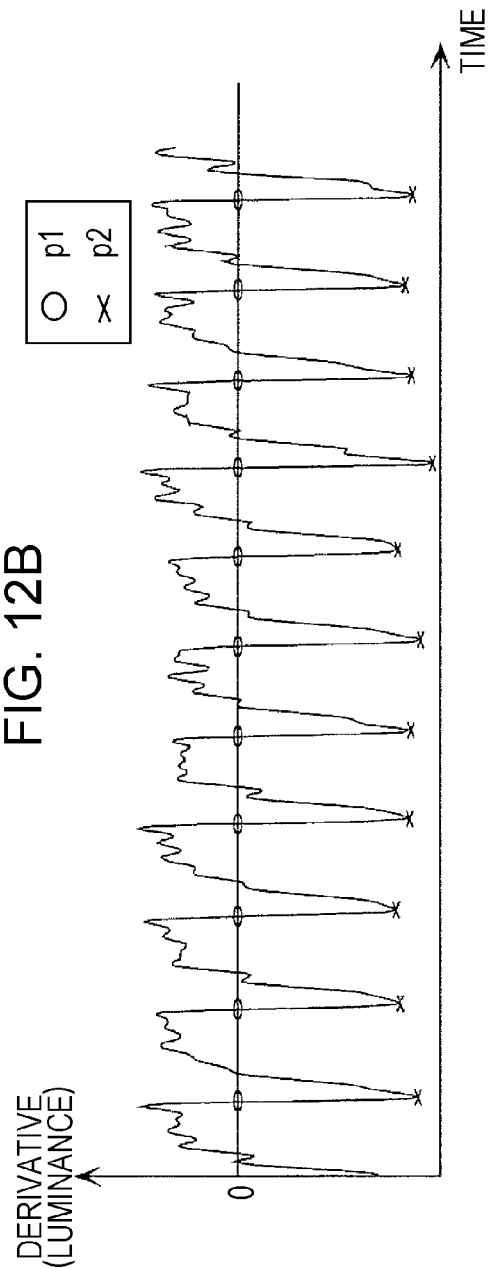

| FACTOR | MAGNIFICATION |
|---|---|
| DASHBOARD: WHITE | 1.2 |
| HOOD: WHITE | 1.2 |
| ROOF: PROVIDED | 2 |
| - - | - - |

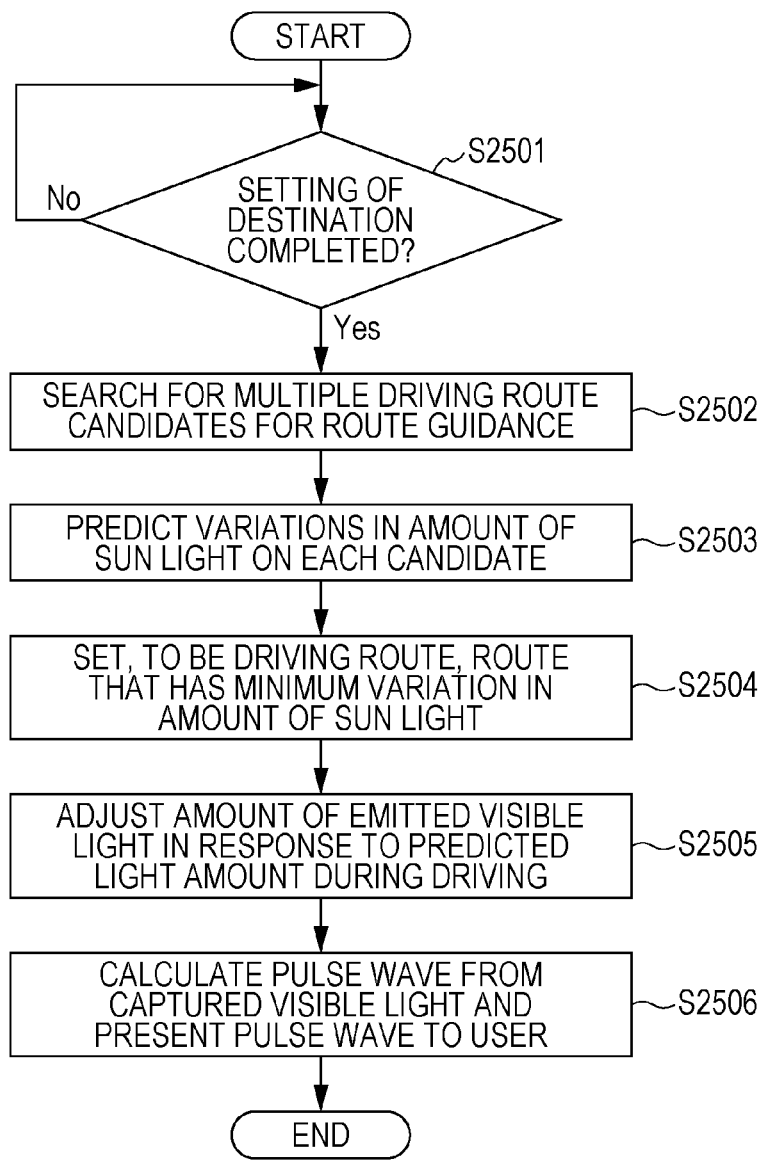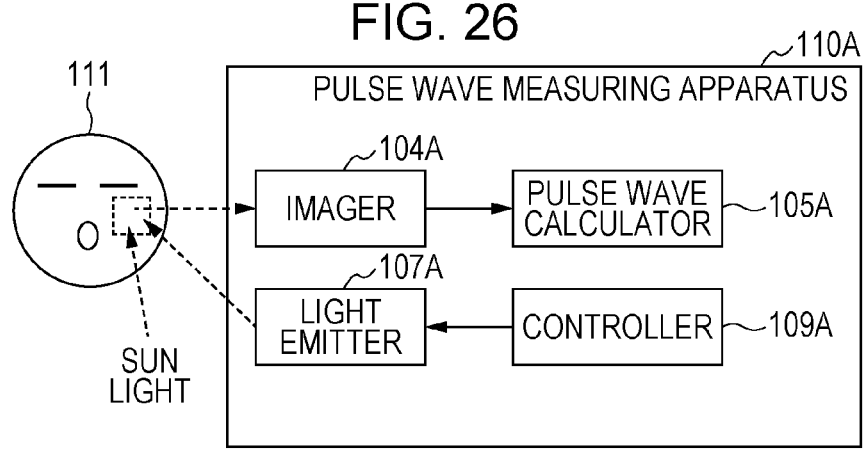

PULSE WAVE MEASURING APPARATUS, CONTROL METHOD, AND NON-TRANSITORY COMPUTER-READABLE RECORDING MEDIUM

BACKGROUND

1. Technical Field

The present disclosure relates to a pulse wave measuring apparatus, a control method, and a non-transitory computer-readable recording medium.

2. Description of the Related Art

Japanese Unexamined Patent Application Publication No. 8-159800 discloses a technique that selects from multiple driving routes a route along which a driver may drive a car avoiding the glare of the sun. Japanese Unexamined Patent Application Publication No. 2000-353295 discloses a technique that guides a driver driving a car that uses sun light to a route where a lot of sun light is available.

In accordance with the technique disclosed in Japanese Unexamined Patent Application Publication No. 8-159800, the driver changes the route if the sun is at a position causing the driver to be in the glare of the sun light. The technique disclosed in Japanese Unexamined Patent Application Publication No. 2000-353295 searches for and guides the user to a route that provides an increased amount of sun light to the car capable of generating solar power when the car needs sun light.

The techniques disclosed above do not include a technique of controlling variations in an amount of light illuminating the driver.

SUMMARY

One non-limiting and exemplary embodiment provides a pulse wave measuring apparatus that controls variations in an amount of light illuminating a driver.

In one general aspect, the techniques disclosed here feature a pulse wave measuring apparatus includes a light emitter that illuminates with light having an amount an area containing a part of skin of a user staying in a vehicle, an imager that captures an image of the area, a controller that (A) obtains a driving route from a departure point of the vehicle to a destination point of the vehicle, (B) obtains an estimated time at which the vehicle passes through a location along the driving route, and predicts an incident amount of sun light that enters the vehicle at the location at the estimated time, and (C) calculates the amount under a condition that a sum of the predicted incident amount and the amount is a constant value, and a pulse wave calculator that calculates a pulse wave of the user using the image, and outputs pulse wave information of the user. The controller, when obtaining the driving route, obtains driving route candidates from the departure point to the destination point, obtains a candidate estimated time at which the vehicle passes through a candidate location along each of the obtained driving route candidates, predicts a candidate incident amount of sun light entering the vehicle at the candidate location at the candidate estimated time, and obtains, as the driving route with a higher priority, a driving route candidate having a smaller variation in the predicted candidate incident amount from among the driving route candidates.

It should be noted that general or specific embodiments may be implemented as a system, a method, an integrated circuit, a computer program, a non-transitory computer readable recording medium, or any selective combination thereof. The non-transitory computer readable recording medium may include a non-volatile recording medium, such as a compact disk read-only memory (CD-ROM).

In accordance with the disclosure, variations in an amount of light illuminating a driver are controlled. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8A and FIG. 8B illustrate an example of a method to calculate an incident amount of sun light in accordance with the first embodiment;

FIG. 10A and FIG. 10B illustrate how a pulse wave timing is calculated in accordance with the first embodiment;

FIG. 12A and FIG. 12B illustrate peaks and inflection points of the pulse wave in accordance with the first embodiment;

FIG. 25 is a flowchart illustrating an operation of the pulse wave measuring apparatus of the fifth embodiment; and FIG. 26 is a block diagram of a pulse wave measuring apparatus in accordance with a modification of each embodiment.

DETAILED DESCRIPTION

Figure 1:
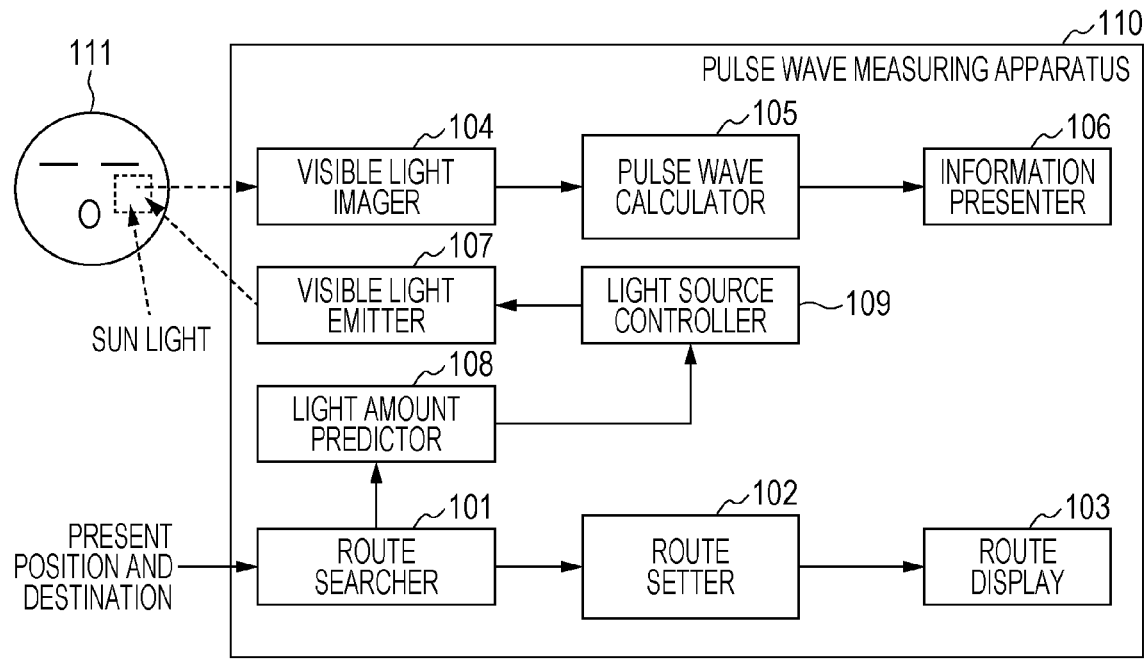
FIG. 1 is a block diagram of a pulse wave measuring apparatus of a first embodiment.

Underlying Knowledge Forming Basis of the Present Disclosure

According to one aspect of the disclosure, a pulse wave measuring apparatus includes a light emitter that illuminates with light having an amount an area containing a part of skin of a user staying in a vehicle, an imager that captures an image of the area, a controller that (A) obtains a driving route from a departure point of the vehicle to a destination point of the vehicle, (B) obtains an estimated time at which the vehicle passes through a location along the driving route, and predicts an incident amount of sun light that enters the vehicle at the location at the estimated time, and (C) calculates the amount under a condition that a sum of the predicted incident amount and the amount is a constant value, and a pulse wave calculator that calculates a pulse wave of the user using the image, and outputs pulse wave information of the user. The controller, when obtaining the driving route, obtains driving route candidates from the departure point to the destination point, obtains a candidate estimated time at which the vehicle passes through a candidate location along each of the obtained driving route candidates, predicts a candidate incident amount of sun light entering the vehicle at the candidate location at the candidate estimated time, and obtains, as the driving route with a higher priority, a driving route candidate having a smaller variation in the predicted candidate incident amount from among the driving route candidates.

According to the above aspect of the disclosure, when the incident amount of the sun light varies in the driving route from the departure point to the destination point of the driving route, the light emitter in the pulse wave measuring apparatus varies the amount of light emitted thereby such that the total variations are controlled. As a result, the light emitter is controlled such that an amount of light illuminating a user is a constant value to obtain the pulse wave of the user. The accuracy of the pulse wave obtained is thus increased. The pulse wave measuring apparatus may control the variations in the amount of light illuminating the user as a driver. In accordance with the above aspect of the disclosure, the pulse wave measuring apparatus selects from among the multiple driving route candidates a driving route having a relatively smaller variation in the incident amount of sun light. In this way, the user drives along the route having a relatively smaller variation in the incident amount of the sun light. The variations in the sun light illuminating the user are thus controlled. The pulse wave measuring apparatus even more controls the variations in the amount of light illuminating the user as the driver.

The controller obtains weather information at the location at the estimated time, adjusts the predicted incident amount in accordance with the weather information, and calculates the amount using the adjusted incident amount.

According to the above aspect of the disclosure, the pulse wave measuring apparatus uses the variations in the incident light of the sun light caused by weather along the route and sets the amount of light illuminating the user to be a constant value to obtain the pulse wave of the user. Even if the weather changes or varies, the pulse wave measuring apparatus may control the variations in the incident amount of the sun light illuminating the user.

The controller obtains structure information of the vehicle, adjusts the predicted incident amount in accordance with the structure information, and calculates the amount using the adjusted incident amount.

According to the above aspect of the disclosure, the pulse wave measuring apparatus accounts for the structure information of the vehicle, and sets the amount of light illuminating the user to be a constant value to obtain the pulse wave of the user. Even if there is a difference or variation in the structure information, the pulse wave measuring apparatus controls the variations in the amount of light illuminating the user.

The controller obtains building information of buildings around the location, adjusts the predicted incident amount in accordance with the building information, and calculates the amount using the adjusted incident amount.

According to the above aspect of the disclosure, the pulse wave measuring apparatus accounts for the building information of the buildings around the location, and sets the amount of light illuminating the user to be a constant value to obtain the pulse wave of the user. Even if there is a difference or variation in the building information, the pulse wave measuring apparatus controls the variations in the amount of light illuminating the user.

According to another aspect of the disclosure, a pulse wave measuring apparatus includes a light emitter that illuminates with light having an amount an area containing a part of skin of a user staying in a vehicle, an imager that captures an image of the area, a controller that (D) obtains a present time and a present position of the vehicle, and estimates an incident amount of sun light that enters the vehicle at the present position at the present time, and (E) calculates the amount under a condition that a sum of the estimated incident amount and the amount is a constant value, and a pulse wave calculator that calculates a pulse wave of the user using the image, and outputs pulse wave information of the user.

According to the above aspect of the disclosure, the light emitter in the pulse wave measuring apparatus varies the amount of light emitted thereby such that variations in the incident amount of the sun light at the present position at the present time are controlled. As a result, an amount of light illuminating a user is set to be a constant value to obtain the pulse wave of the user. The accuracy of the pulse wave obtained is thus increased. The pulse wave measuring apparatus may control the variations in the amount of light illuminating the user as a driver.

According to another aspect of the disclosure, a control method includes obtaining a driving route from a departure point of a vehicle to a destination point of the vehicle, obtaining an estimated time at which the vehicle passes through a location along the driving route, predicting an incident amount of sun light entering the vehicle at the location at the estimated time, calculating an amount of light emitted from a light emitter under a condition that a sum of the incident amount and the amount is a constant value, causing the light emitter at the location to emit light at the amount to illuminate an area containing skin of a user staying in the vehicle, obtaining an image containing an image of the skin, calculating a pulse wave of the user using the image, and outputting information related to the pulse wave.

According to the above aspect, the control method provides the same effect as the pulse wave measuring apparatus.

According to another aspect of the disclosure, a control method includes obtaining a present time and a present position of a vehicle, estimating an incident amount of sun light entering the vehicle at the present position at the present time, calculating an amount of light emitted from a light emitter under a condition that a sum of the incident amount and the amount is a constant value, causing the light emitter to emit light at the amount to illuminate an area containing skin of a user staying in the vehicle, obtaining an image containing an image of the skin, calculating a pulse wave of the user using the image, and outputting information related to the pulse wave.

According to the above aspect, the control method provides the same effect as the pulse wave measuring apparatus.

According to another aspect of the disclosure, a non-transitory computer-readable recording medium stores a computer program causing a computer to perform the control method.

According to the above aspect, the non-transitory computer-readable recording medium provides the same effect as the pulse wave measuring apparatus.

General or specific embodiments may be implemented as a system, a method, an integrated circuit, a computer program, a non-transitory computer readable recording medium, or any selective combination thereof.

Embodiments are specifically described with reference to the drawings.

Each of the embodiments described below represents a general or specific example of the disclosure. Numerical values, shapes, materials, elements, layout positions of the elements, connection forms, steps, and the order of the steps in the embodiments are described for exemplary purposes only, and are not intended to limit the disclosure. Elements not described in independent claims indicative of a generic concept, from among the elements of the embodiments, may be any elements.

First Embodiment

A pulse wave measuring apparatus 110 of the first embodiment is described below. The pulse wave measuring apparatus 110 controls variations in an amount of light illuminating a driver. More specifically, the pulse wave measuring apparatus 110 of the first embodiment obtains a pulse wave of a user (driver) using sun light entering a vehicle, and light emitted from a light source inside the vehicle. The pulse wave measuring apparatus 110 of the first embodiment may be a standalone device or may be implemented as a vehicle navigation device with a functionality of the pulse wave measuring apparatus. In the discussion that follows, the pulse wave measuring apparatus is implemented as a vehicle navigation device with a functionality of the pulse wave measuring apparatus.

Figure 2:
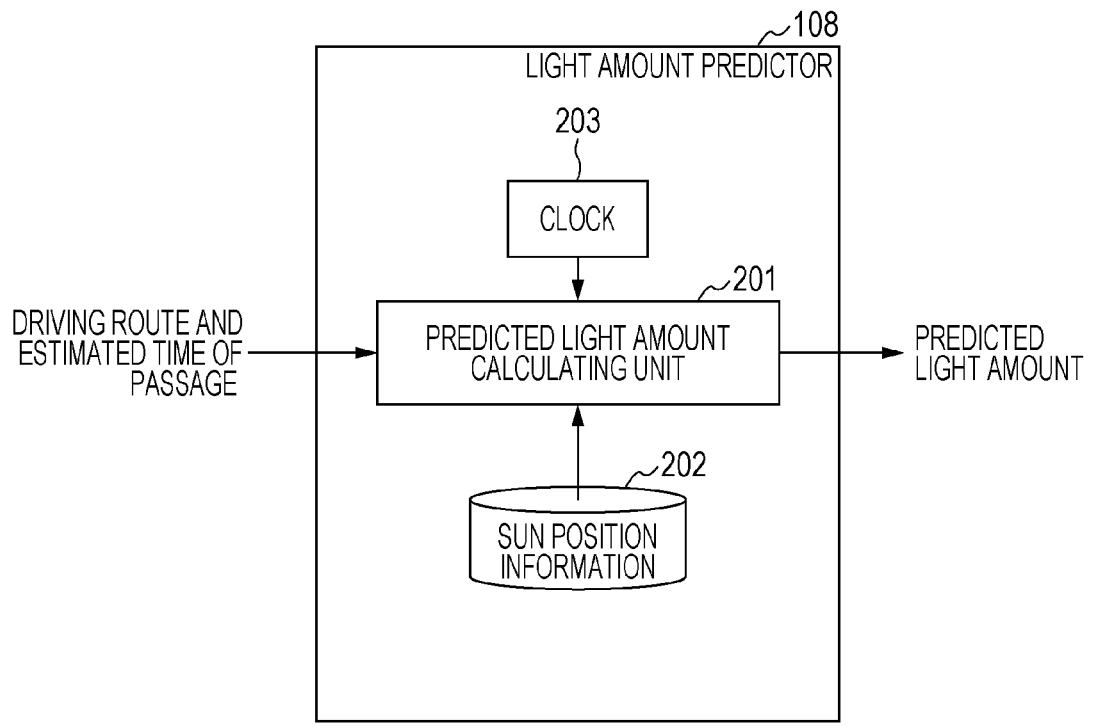
FIG. 2 is a detailed block diagram of a light amount predictor in the pulse wave measuring apparatus of the first embodiment.
Figure 3:
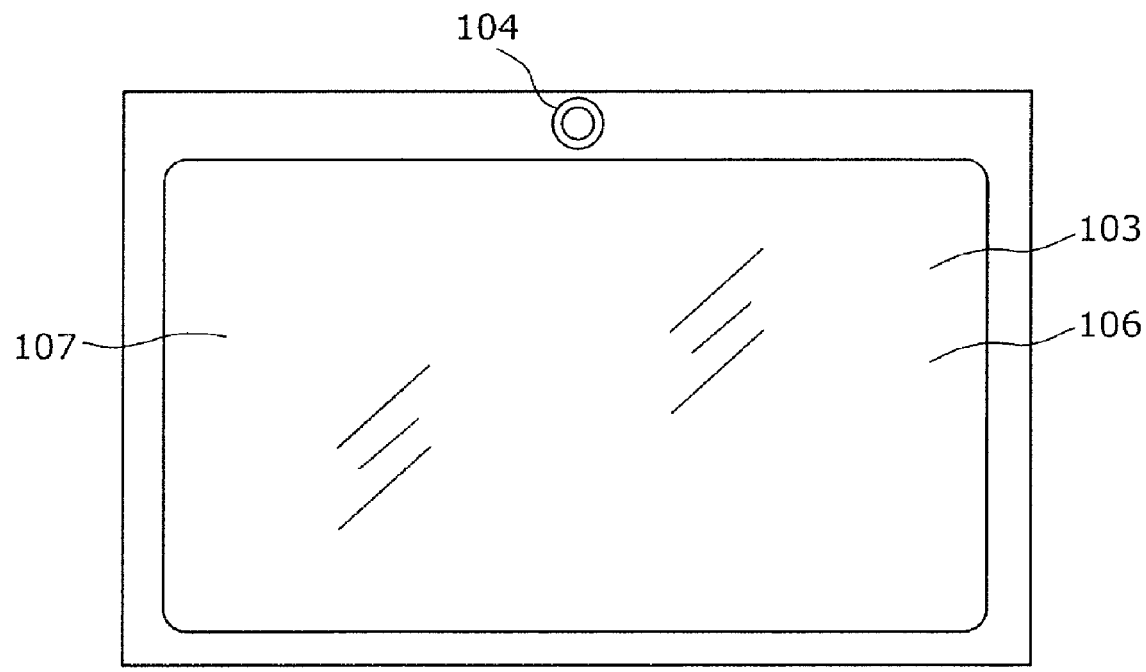
FIG. 3 is an external view of the pulse wave measuring apparatus of the first embodiment.

FIG. 1 is a block diagram of the pulse wave measuring apparatus 110 of the first embodiment. FIG. 2 is a detailed block diagram of a light amount predictor 108 of the first embodiment. FIG. 3 is an external view of the pulse wave measuring apparatus 110 of the first embodiment.

Referring to FIG. 1, the pulse wave measuring apparatus 110 includes a route searcher 101, a route setter 102, a route display 103, a visible light imager 104, a pulse wave calculator 105, an information presenter 106, a visible light emitter 107, a light amount predictor 108, and a light source controller 109.

The route searcher 101 searches for a driving route from a departure point as a present position to a destination point.

The route setter 102 sets a searched route to be a driving route.

The route display 103 presents the set route to a user.

The visible light imager 104 captures visible light reflected from the skin of a user 111 when sun light and light emitted by the visible light emitter 107 illuminate the skin of the user 111.

The pulse wave calculator 105 extracts a pulse wave feature quantity from an image captured using visible light.

The information presenter 106 presents pulse wave information to the user.

The visible light emitter 107 is a light source that emits visible light to illuminate the user 111.

The light amount predictor 108 predicts an amount of sun light illuminating the user 111 during driving along the driving route received from the route searcher 101.

In response to the prediction results, the light source controller 109 controls an amount of light of the visible light emitter 107.

These elements are housed in the casing of the pulse wave measuring apparatus 110. Referring to FIG. 3, the route display 103, the visible light imager 104, the information presenter 106, and the visible light emitter 107 are mounted in a manner such that those elements are exposed to the outside of the casing. For example, the visible light imager 104 is mounted on the top portion of the casing, and the route display 103, the information presenter 106, and the visible light emitter 107 are mounted as a display of the pulse wave measuring apparatus 110.

Route Searcher

When the user 111 as a driver, or a fellow passenger issues an instruction to set a route, the route searcher 101 receives the vehicle's present position and departure point, and searches for a route from the present position as a departure point to a destination point in view of the estimated time of arrival at the destination point and an easy-to-drive route (free from heavy traffic and having a larger width). The method of searching route may be one of related-art techniques, such as the Dijkstra's algorithm and the extended Dijkstra's algorithm.

Route Setter

The route setter 102 presents to the user 111 (driver) or the fellow passenger (not illustrated) routes searched by the route searcher 101, and sets the route selected by the user 111 to be a driving route (also referred to as a guidance route or route).

Route Display

The route display 103 displays the guidance route set by the route setter 102, and performs control related to displaying.

Visible Light Emitter

The visible light emitter 107 emits light in the visible light region to illuminate an area containing at least the skin of the user 111 in the vehicle. The light source controller 109 controls the operation of the visible light emitter 107 as to whether light is to be emitted or not, and an amount of light emitted by the visible light emitter 107. More specifically, the visible light emitter 107 emits light in a wavelength range from 400 to 800 nm, and is implemented as a display of a vehicle navigation system of FIG. 3. Alternatively, the visible light emitter 107 may emit an infrared light ray together with a visible light ray. Alternatively, an infrared light emitter may be employed instead of the visible light emitter 107. The visible light emitter 107 and the infrared light emitter are collectively referred as a light emitter.

Figure 4:
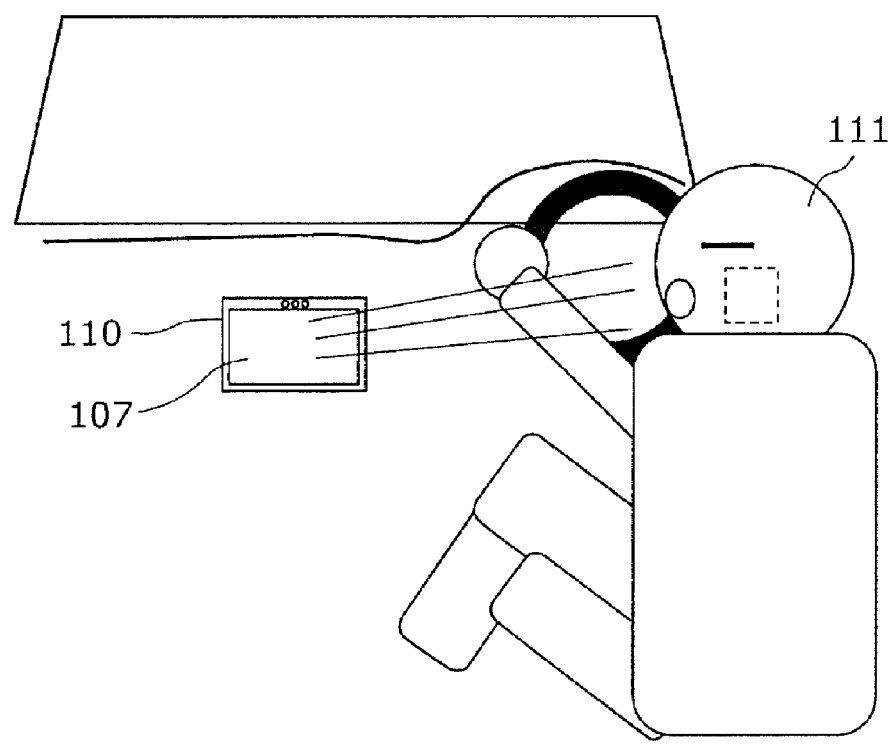
FIG. 4 illustrates an operational scene of the pulse wave measuring apparatus of the first embodiment.

An operational scene with the visible light emitter 107 implemented by the display of the vehicle navigation apparatus is described below. FIG. 4 illustrates the operational scene of the pulse wave measuring apparatus 110 of the first embodiment;

As illustrated in FIG. 4, the pulse wave measuring apparatus 110 is mounted on the center of the dashboard of a vehicle in the same way as a related-art vehicle navigation apparatus. When the visible light emitter 107 emits light from the center of the dashboard, the light illuminates the cheeks of the user 111 where a pulse wave from the face of the user 111 is easy to obtain. More specifically, the light from the visible light emitter 107 illuminates half of the face of the user 111. If the user 111 is a driver, and the vehicle is of right-hand drive type, the light from the visible light emitter 107 illuminates the left half of the face of the user 111. If the vehicle is a left-hand drive type, the light from the visible light emitter 107 illuminates the right half of the face of the user 111.

The user 111 may manually control the amount of light using a controller. Alternatively, the user 111 may manually control the direction of the light from the visible light emitter 107. A universal joint mechanism may be mounted on the rear side of the pulse wave measuring apparatus 110. The user 111 may manually move the pulse wave measuring apparatus 110 to adjust the orientation (tilt angle) of the pulse wave measuring apparatus 110 such that the light illuminates the user 111. The amount of light illuminating the user 111 is adjusted even when the driver changes his or her face in position. The position of the face of the driver may typically change depending on whether the driver is a man or a woman. The pulse wave is more accurately detected by allowing the driver to change the orientation of the screen.

The pulse wave measuring apparatus 110 uses the display of the vehicle navigation apparatus as a light source of visible light. Alternatively, an auxiliary lighting device of visible light may be mounted on the side of the vehicle navigation apparatus. The display of the vehicle navigation apparatus is typically used to check a map or the present position. The lighting device of visible light may illuminate the area of the cheeks of the user 111. If the amount (intensity) of light of the display of the vehicle navigation apparatus is not sufficient, the lighting device of visible light may be additionally mounted. The user 111 may adjust the direction of visible light, and the map on the vehicle navigation apparatus is easy to view while the ease and accuracy of the adjustment of the amount of illumination light are ensured.

Figure 5:
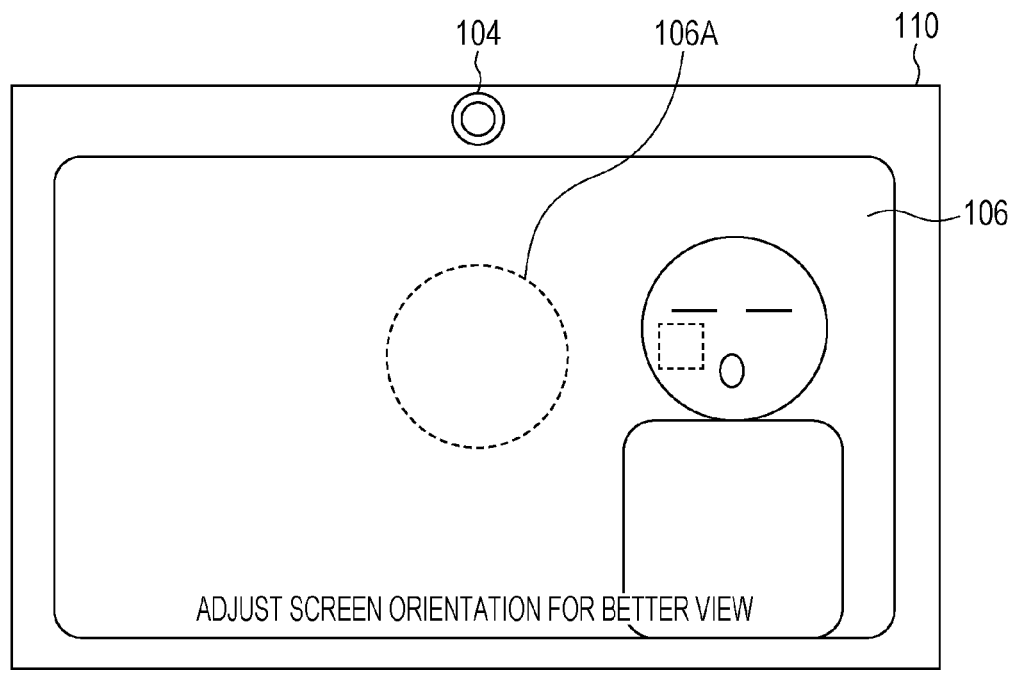
FIG. 5 illustrates an example of guidance information to adjust an orientation of the pulse wave measuring apparatus of the first embodiment.

Guidance information to update the orientation of the pulse wave measuring apparatus 110 may be presented to the user 111. FIG. 5 illustrates an example of the guidance information to adjust the orientation of the pulse wave measuring apparatus 110 of the first embodiment.

When a specific period of time (for example, 10 seconds) has elapsed since a signal enabling the visible light emitter 107 to be controlled was sent to the light source controller 109, the information presenter 106 may instruct the display to be adjusted in orientation as illustrated in FIG. 5. Referring to FIG. 5, a target position of the face of the user 111 is displayed on a center portion 106A of the display, and the user 111 may be instructed to adjust the pulse wave measuring apparatus 110 in orientation and position such that the face of the user 111 is located at the center portion 106A. This arrangement is useful when the user 111 is at a loss for what to do with the pulse wave measuring apparatus 110 in orientation.

The pulse wave measuring apparatus 110 is typically mounted near or at the center of the dashboard of the vehicle. The mounting position of the pulse wave measuring apparatus 110 is not limited to the center of the dashboard. For example, the pulse wave measuring apparatus 110 may be mounted in front of the user 111. In this case, the visible light emitter 107 illuminates the user 111 from the front side, namely, illuminates the entire face of the user 111 rather than half of the face of the user 111. In this way, the area of the face of the user 111 from which the pulse wave is acquired becomes wider, and the pulse wave is accurately obtained. If the pulse wave measuring apparatus 110 is mounted at the center of the dashboard of the vehicle and when it is light during the daytime, half of the face of the user 111, typically the side of the face opposite from the window side of the vehicle is illuminated. But there are times when the amount of illumination light is insufficient, and the pulse wave is difficult to obtain. If the pulse wave measuring apparatus 110 is mounted right in front of the user 111 when seated, the pulse wave may be obtained from the side of the face on the window side of the vehicle.

The user 111 adjusts the pulse wave measuring apparatus 110 in orientation such that the visible light emitter 107 emits light to illuminate the face of the user 111. The disclosure is not limited to this method.

Figure 6A:
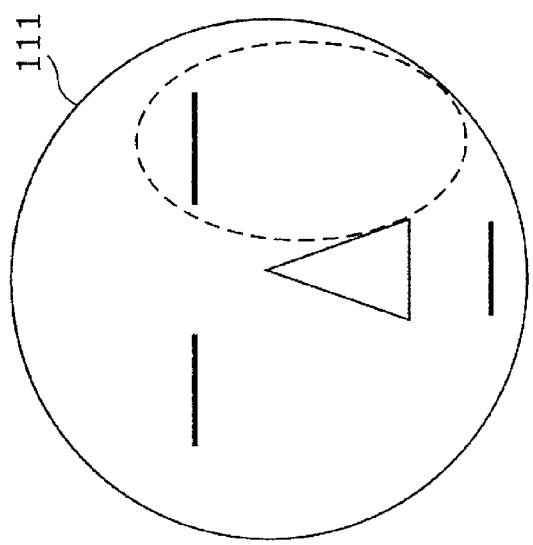
FIG. 6A and FIG. 6B illustrate illumination areas that a visible light emitter illuminates.
Figure 6B:
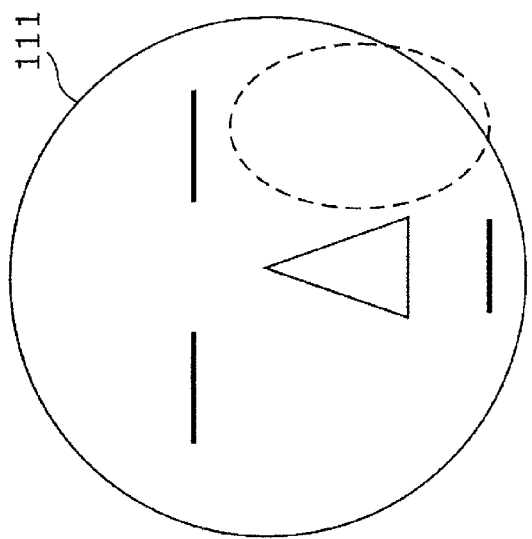

FIG. 6A and FIG. 6B illustrate illumination areas that the visible light emitter 107 illuminates with light. Referring to FIG. 6A and FIG. 6B, elliptical shapes defined by broken line indicate the illumination areas the visible light emitter 107 illuminates.

When the user 111 drives a vehicle, the visible light emitter 107 emits light, illuminating the eyes of the user 111 as illustrated in FIG. 6A. The user 111 may feel the glare, possibly causing an accident. If the user 111 has the opportunity to adjust the orientation of the pulse wave measuring apparatus 110 in advance, the user 111 sets the center of a light beam emitted from the visible light emitter 107 to focus on an area below the center portion of a cheek that the user 111 has originally intends to illuminate as illustrated in FIG. 6B. Thus, one cheek of the user 111 is illuminated more strongly, and an eye and the area about the eye are relatively illuminated more weakly. The user 111 is thus able to adjust illuminance with nothing interfering with driving.

An amount of light emitted by the visible light emitter 107 may suddenly increase during driving. In such a case, facial recognition is performed with the visible light imager 104 in advance. The visible light emitter 107 illuminates the face of the user 111, starting with the cheek to the chin while expanding the illumination area, and then stopping illuminating before reaching the eye. More specifically, a base level of a luminance value signal to the eye used in the facial recognition is not increased.

Light Amount Predictor

The route searcher 101 searches for routes, and the user 111 drives the vehicle along the determined guidance route. The light amount predictor 108 predicts how much sun light enters the vehicle.

As illustrated in FIG. 2, the light amount predictor 108 includes a predicted light amount calculating unit 201, sun position information 202, and a clock 203.

The sun position information 202 includes information indicating the position of the sun at each moment (solar elevation angle (degrees), and solar azimuth angle (degrees)).

The clock 203 measures time and date.

The predicted light amount calculating unit 201 predicts an amount of the sun light along the driving route during driving, based on the guidance route provided by the route searcher 101, an estimated time of passage at each point along the guidance route, and the position of the sun at each point at the estimated time of passage (solar elevation angle (degrees), and solar azimuth angle (degrees)).

The process of the light amount predictor 108 is described in detail below.

Figure 7A:
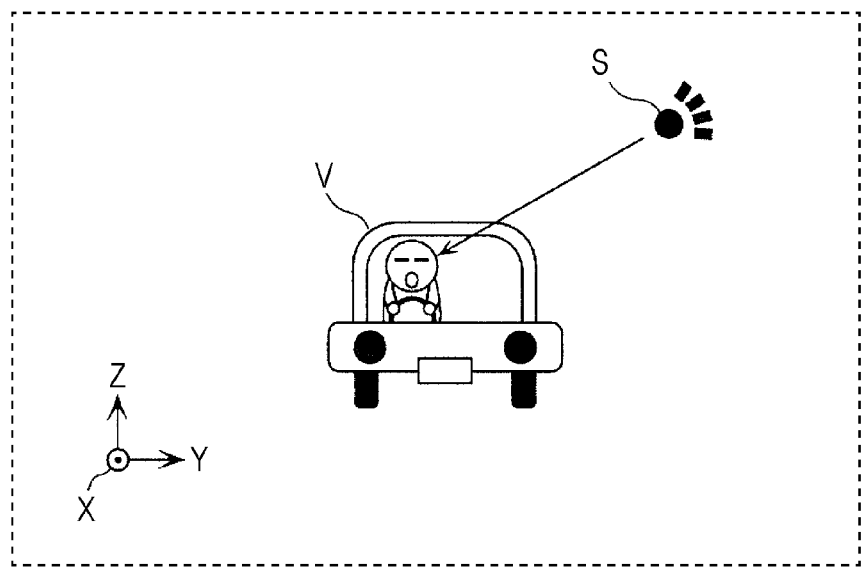
FIG. 7A through FIG. 7C illustrate sun light that enters a vehicle in accordance with the first embodiment.
Figure 7B:
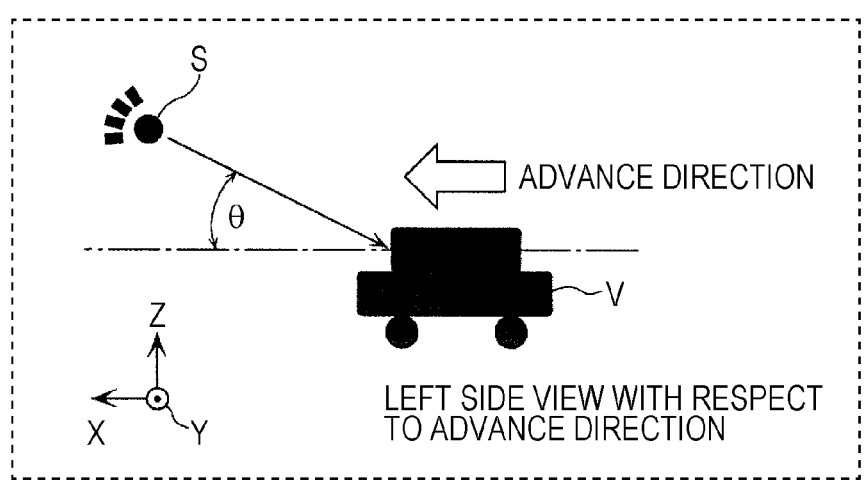
Figure 7C:
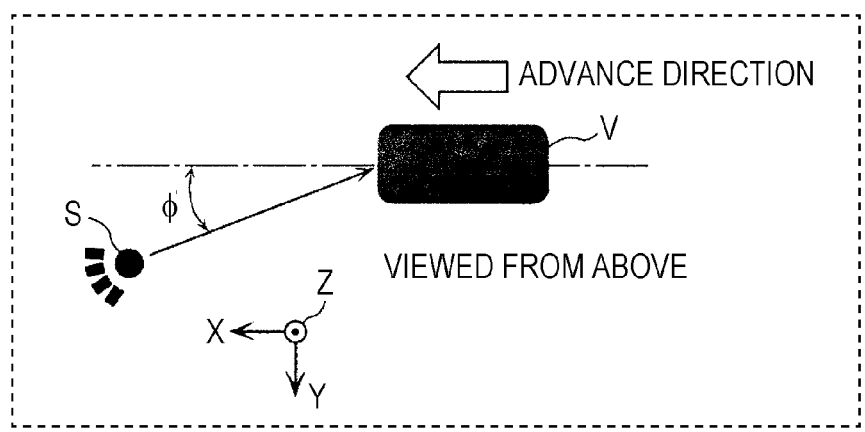

FIG. 7A through FIG. 7C illustrate an amount of the sun light that enters a vehicle V. Referring to FIG. 7A, the advance direction of the vehicle V is aligned with a positive direction of an X axis, a direction perpendicularly crossing the advance direction of the vehicle V from right to left is aligned with a positive direction of a Y axis, and a vertically upward direction from the user 111 is aligned with a positive direction of a Z axis. The Y axis positive direction and the Y axis negative direction are respectively referred to the left direction and the right direction. The Z axis positive direction and the Z axis negative direction are respectively referred to as the upward direction and the downward direction.

FIG. 7A, FIG. 7B, and FIG. 7C are respectively a diagrammatic view of a positional relationship between the vehicle V and the sun S viewed from the advance direction of the vehicle V, a diagrammatic view of the positional relationship viewed from the left hand of the vehicle V, and a diagrammatic view of the positional relationship viewed from above the vehicle V. As illustrated in the left-side view of FIG. 7B, the sun light from the sun S illuminates the vehicle V at an angle of θ with respect to the X axis positive direction if viewed from the left hand side. As illustrated in the top view of FIG. 7C, the sun light from the sun S illuminates the vehicle V at an angle φ with respect to the X axis positive direction if viewed from above.

FIG. 8A and FIG. 8B illustrate an example of a method to calculate an incident amount of sun light in accordance with the first embodiment. Referring to FIG. 8A and FIG. 8B, an amount of the sun light directly (direct sun light) illuminating a plane U having a unit area containing an origin O and parallel with a YZ plane is considered.

FIG. 8A illustrates the sun light that is incident on the plane U in a direction, normal to the plane U, along the X axis positive direction. Let 1 represent an amount of light illuminating the plane U, and serves as a reference of an amount of light.

FIG. 8B illustrates the sun light from the sun S at an direction SD illuminating the plane U. The direction SD is obtained by rotating a line extending along the X axis positive direction by an angle θ about the origin O toward the Z axis positive direction, and then by rotating the line by an angle φ toward the Y axis positive direction. In other words, the direction SD, if projected onto a plane parallel with the XZ plane (an XZ plane of projection), makes an angle θ with respect to the X axis positive direction, and, if projected onto a plane parallel with the XY plane (an XY plane of projection), makes an angle φ with respect to the X axis positive direction, An amount of light illuminating the plane U is calculated described below.

As described above, the sun light is incident on the plane U in the direction SD that makes the angle θ with respect to the X axis positive direction on the XZ plane of projection, and makes the angle φ with respect to the X axis positive direction on the XY plane of projection. The amount of light illuminating the plane U is smaller than the amount of light incident on the plane U as illustrated in FIG. 8A by cos θ on the XZ plane of projection, and by cos φ on the XY plane of projection. In other words, the amount of light incident on the plane U is equal to an amount of light that is incident on a plane UA having an area of cos θ×cos φ. The amount of light incident on the plane U is cos θ×cos φ, namely, is the amount of light incident on the plane U of FIG. 8A multiplied by cos θ×cos φ.

The sun light entering the vehicle V contains scattered light in addition to the direct sun light. The scattered light does not dependent on the direction made by the vehicle V and the sun S, but on the time band of the day and weather. The light amount predictor 108 calculates a sum of the amount of the direct sun light and the scattered light as an amount of the sun light entering the vehicle V.

The route searcher 101, the route setter 102, and the light amount predictor 108 may be collectively referred to as a controller. More specifically, the controller (A) obtains a driving route from a departure point to a destination point of the vehicle V, (B) obtains an estimated time of passage of the vehicle V that passes through a location along the driving route, and predicts an incident amount of sun light that enters the vehicle V at the location at the estimated time of passage, and (C) controls an amount of light of the light emitter at the location by calculating the amount of light of the light emitter such that a sum of the predicted incident amount of the sun light and the amount of light of the light emitter is a constant value.

Light Source Controller

The light source controller 109 controls the amount of light of the visible light emitter 107 (more specifically, as to whether the visible light emitter 107 is to emit light, and an amount of light if the visible light emitter 107 is going to emit light).

More specifically, based on the predicted amount of light obtained from the light amount predictor 108, the light source controller 109 controls an amount of light of the visible light emitter 107 such that the following equation (1) holds.

$$\text{Predicted light amount} + \text{amount of light of the visible light emitter 107} = \text{constant value} \quad (1)$$

If the predicted amount of light is x lux, and the constant value of the total amount of light is 1000 lux, the calculated amount of light from the visible light emitter 107 is (1000−x) lux. The light source controller 109 controls the visible light emitter 107 such that the visible light emitter 107 outputs the calculated amount of light. The light source controller 109 controls the visible light emitter 107 by referencing a table (not illustrated) that lists a relationship between an amount of emitted light and a current value or a voltage value.

The constant value is determined based on the guidance route set by the route setter 102. The constant value is described further in detail below.

The word "constant" is intended to express not only "something that is exactly constant" but also "something that falls within a certain range (for example, a range within several percent from a rated value). The same is true of the other values.

Visible Light Imager

The visible light imager 104 obtains an image of an area containing the skin of the user 111. The light from the sun and the light from the visible light emitter 107 illuminate the skin of the user 111. The visible light imager 104 receives light reflected from the skin of the user 111. The visible light imager 104 obtains a skin image that is a color image of the skin containing the face and the hands of the user 111. The skin image is obtained by consecutively imaging the same location of the user 111 by multiple timings in time sequence. The skin image may include a video or multiple still images.

The visible light imager 104 may obtain the skin image by imaging the skin, or by receiving data of the skin image from another apparatus that has captured images. To image the skin, the visible light imager 104 may be implemented by a camera including an image sensor, such as a charge-coupled device (CCD) or a complementary metal oxide semiconductor (CMOS) image sensor.

By using a filter on the image sensor, the visible light imager 104 obtains light falling within a visible light range of 400 to 800 nm, and thus obtains three signals, namely, red, green, and blue (RGB) signals.

Pulse Wave Calculator

The pulse wave calculator 105 calculates the pulse wave of the user 111 in accordance with the image, and outputs pulse wave information of the user 111.

More specifically, the pulse wave calculator 105 extracts a pulse wave from the skin image obtained by the visible light imager 104, and calculates a feature quantity of the pulse wave. The pulse wave calculator 105 obtains a timing of the pulse wave as the feature quantity of the pulse wave in the visible light region, and calculates the heartbeat interval from adjacent timings of the pulse wave in time sequence. More specifically, the pulse wave calculator 105 obtains the timings of the pulse wave (hereinafter referred to as pulse wave timings), based on luminance variations with respect to the time sequence in the multiple images. To obtain the pulse wave timings, the pulse wave calculator 105 obtains each skin image by associating each skin image with a time point at which each skin image has been captured.

The pulse wave calculator 105 identifies a location having a maximum luminance variation in the skin images, and calculates a pulse wave timing using a luminance waveform at the identified location with respect to time. Using pre-stored patterns of faces and hands, the pulse wave calculator 105 identifies the location of the face or the hands in the skin images, and calculates the pulse wave timing using a time waveform of luminance at the identified location. The pulse wave timing is thus is thus obtained. The pulse wave timing refers to a specific time point on a time waveform of luminance, namely, a time at a specific position on the time waveform of luminance. Related art local search, such as hill climbing technique, auto-correlation technique, or a technique of using a derivative function, may be used to obtain a peak position in the time waveform (namely, peak searching). A specific hardware example of the pulse wave calculator 105 is a CPU.

When the heart contracts, blood is pushed out of the heart, and distributed through the face, the hands, and other parts. Depending on components in the blood, such as hemoglobin, the luminance of the face or the hands in the captured image varies. In other words, information related to the flow of the blood is obtained from luminance variations of the face or the hands in time sequence in the image. The pulse wave calculator 105 obtains the pulse wave timing as such information.

The pulse wave timing may be obtained from within the visible light region, using luminance of a green wave length band in the skin image. This is because in the image captured using light containing the visible light wage length, a large magnitude of variation appears in information of the wave length band at or near green light. In an image having multiple pixels, the luminance of green wavelength at pixels corresponding to the face or the hands into which a larger amount of blood flows is lower than the luminance of green wavelength at pixels corresponding to the face or the hands into which a smaller amount of blood flows.

Figure 9:
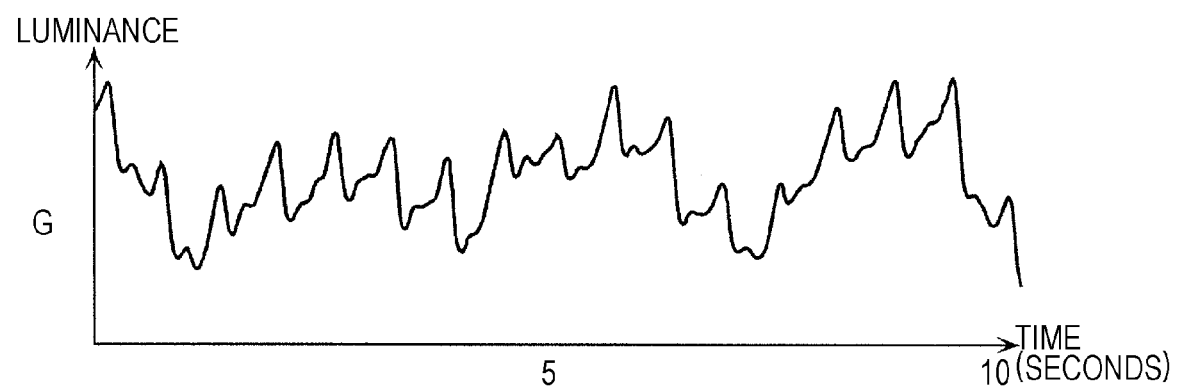
FIG. 9 illustrates an example of a pulse wave extracted by a pulse wave calculator of the first embodiment.

FIG. 9 illustrates an example of a luminance variation in the visible light region, in particular, a luminance variation in the green light, in the skin image, in accordance with the first embodiment. More specifically, FIG. 9 illustrates the luminance variation in the green light component (G) of the cheek in the skin image of the visible light region captured by the visible light imager 104. In FIG. 9, the abscissa represents luminance, and the ordinate represents time. As illustrated in FIG. 9, the luminance variation is attributed to the pulse wave, and the luminance periodically varies.

When the skin is imaged in the visible light region under daily life environment, the skin image contains noise because of a variety of causes including scattered light from illumination. Signal processing, such as filtering, is performed on the captured image to obtain a skin image containing signal variations attributed to the pulse wave. The filter used in this case is a low-pass filter. In accordance with the first embodiment, the luminance variation in the low-pass filtered green light (G) is used.

FIG. 10A illustrates an example of the pulse wave timing calculated in accordance with the first embodiment. Referring to FIG. 10A, the ordinate represents luminance, and the abscissa represents time. The time waveform of FIG. 10A, times t1 through t5 are inflection points or peaks. Each of times t1 through t5 is an inflection point or a peak (a top point or a valley point). In each point included in the time waveform, a first point (top point) having higher luminance than any point prior to or subsequent to the first point or a second point (valley point) having lower than any point prior to or subsequent to the second point is the pulse wave timing.

A method of identifying the position of the peak using the time waveform of FIG. 10A, namely, a peak search method is described below. In the time waveform of luminance of FIG. 10A, t2 may now be a present reference point. The point at time t2 is compared with the point at time t1 immediately prior to time t2, and compared with the point at time t3 immediately subsequent to time t2. If the luminance of the reference point is higher than the luminance at each of the points at the prior time and the subsequent time, the reference point is determined to be positive. In other words, the reference point is a peak, and time of the reference point is determined to be a pulse wave timing. If the luminance of the reference point is lower than the luminance at least one of the points at the prior time and the subsequent time, the reference point is determined to be negative. In other words, the reference point is not a peak, and the time of the reference point is not determined to be a pulse wave timing.

Referring to FIG. 10A, the luminance at time t2 serving as the reference point is higher than the luminance at time t1, but lower than the luminance at time t3. The reference point is determined to be negative. The reference point is incremented by one, and is thus the point at time t3. The luminance at time t3 is higher than the luminance at time t2 prior to time t3, and is higher than the luminance at time t4 subsequent to time t3. The reference point is determined to be positive. The route display 103 obtains as the pulse wave timing the time of the point that is determined to be positive.

The pulse wave timing may be obtained in view of the basic knowledge of the typical pulse wave (for example, 60 to 80 bpm) with the heartbeat interval ranging from 333 to 1000 ms. In this way, the luminance comparison operation described above is not necessarily performed on all the points. If the luminance comparison operation may be performed on some points, an adequate pulse wave timing is thus obtained. More specifically, each point that falls within a range of 333 ms to 1000 ms down to the latest obtained pulse wave timing is used at a reference point, and the luminance comparison operation may be performed on each point. In this case, the next pulse wave timing may be obtained without performing the luminance comparison operation on the points before that range. The pulse wave timing is thus obtained in a way robust to the daily life environment.

Figure 11:
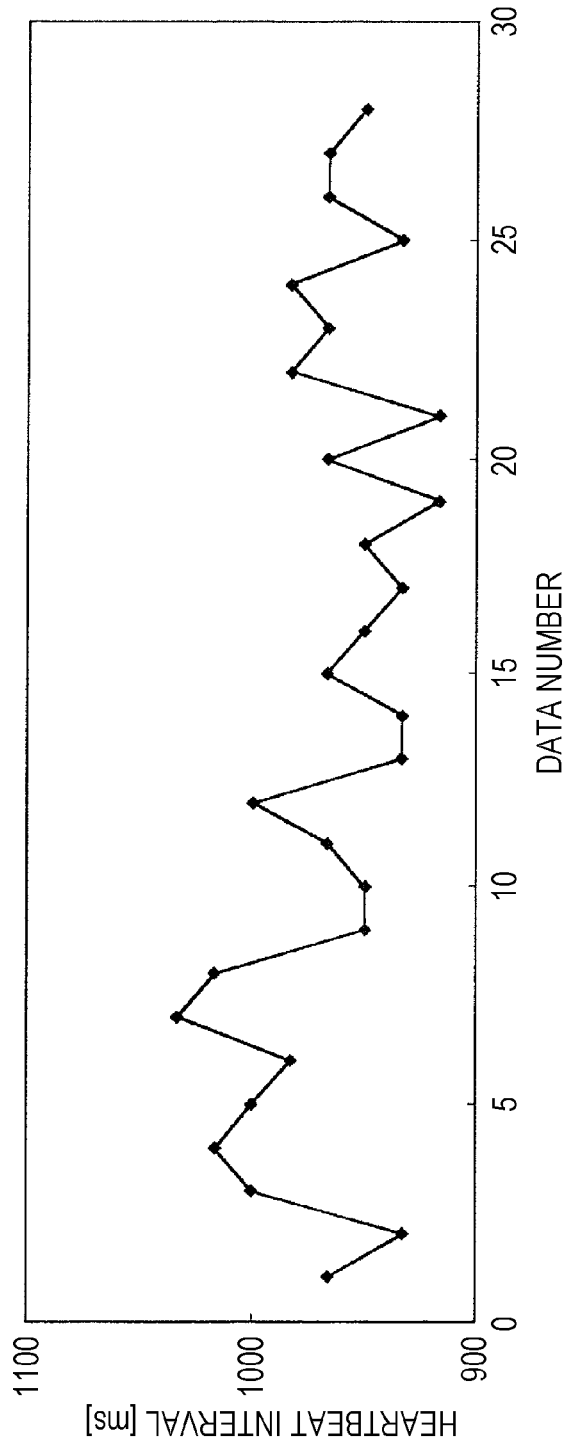
FIG. 11 illustrates a heartbeat interval in accordance with the first embodiment.

The pulse wave calculator 105 calculates a heartbeat interval time from a difference between two adjacent pulse wave timings. The heartbeat interval time varies in time sequence. FIG. 11 illustrates the heartbeat interval time in accordance with the first embodiment. The abscissa represents data numbers arranged in time sequence, and the ordinate represents the heartbeat interval time. FIG. 11 indicates that the heartbeat interval time obtained from the pulse wave varies in time sequence.

The pulse wave calculator 105 extracts an inflection point timing immediately subsequent to the pulse wave timing. More specifically, the pulse wave calculator 105 calculates a first order differential value of the luminance of the pulse wave, obtains a minimum value of the differentiated luminance of the visible light, and sets the timing of the minimum value to be an inflection timing.

The inflection point timing may be obtained, based on the knowledge of the typical pulse wave with the peak interval ranging from 333 to 1000 ms.

FIG. 12A and FIG. 12B illustrate how the inflection point is extracted from the pulse wave. FIG. 12A plots the luminance of the pulse wave obtained by the visible light imager 104. FIG. 12B plots first order differential values of the luminance. As illustrated, each circle represents a peak, and a symbol x represents an inflection point. In FIG. 12A, the abscissa represents time while the ordinate represents luminance. In FIG. 12B, the abscissa represents time while the ordinate represents first order differential values of luminance.

The green light of the pulse wave is used as described above. In principle, hemoglobin absorbs light in the green wavelength band, thereby varying the luminance value obtained by the visible light imager 104. More specifically, when hemoglobin absorbs the green light, the luminance value obtained by the visible light imager 104 is reduced by an amount of absorption. Regarding the shape of the pulse wave obtained by the visible light imager 104, a gradient of the pulse wave from a peak to a valley point subsequent to the peak is sharper than a gradient of the pulse wave from a preceding valley point to the peak. The luminance value is likely to be affected by noise during the transition from the valley point to the peak, but is less likely affected by noise during the transition from the peak to the next valley point because of a sharper gradient. For this reason, an inflection point present during the transition from the peak to the valley point is less likely to be affected by nose, and is thus obtained in a stable manner.

In view of the above discussion, the heartbeat interval time may be obtained from a time difference between two inflection points.

The peak of the pulse wave is a point that is immediately prior to the inflection point and has a zero differential value. More specifically, as illustrated in FIG. 12B, a point having a zero differential value immediately prior to the inflection point labeled with an x symbol is a peak labeled with a circle. Based on this feature, the peak to be obtained may be limited to a peak immediately prior to an inflection point.

The pulse wave calculator 105 calculates the gradient from the peak to the valley point of the pulse wave. A larger gradient is better. This is because the sharpness of the peak of the pulse wave is greater as the gradient is larger, and time shift of the pulse wave timing caused by a filtering process or other process becomes smaller.

Information Presenter

The information presenter 106 presents the face image of the user 111 captured by the visible light imager 104, and instructs the user 111 to display the face of the user 111 on the visible light imager 104. The information presenter 106 presents biometric information obtained from the pulse wave calculator 105. The information presenter 106 also displays on a display of the pulse wave measuring apparatus 110 a heart rate obtained by the pulse wave calculator 105, stress index, and/or sleepiness information of the user 111. The visible light emitter 107 illuminates the user 111 with visible light as described above.

The information presenter 106 displays the biometric information on the display of the pulse wave measuring apparatus 110. The operation of the information presenter 106 is not limited to this. For example, the pulse wave measuring apparatus 110 may includes a transmitting unit, and may communicate with a mobile terminal of the user 111 to display the biometric information on the display of the mobile terminal of the user 111. The mobile terminal may include an information storage unit, and may store the obtained biometric information on the information storage unit to allow the user 111 to check the biometric information during, prior to or subsequent to his or her sleep.

The information presenter 106 presents the biometric information obtained from the pulse wave calculator 105. The information presenter 106 is not limited to that operation. For example, the information presenter 106 may present an amount of light of a light source in the visible light emitter 107. Further, the information presenter 106 may display a variation in the amount of light at the present moment in percentage.

Figure 13:
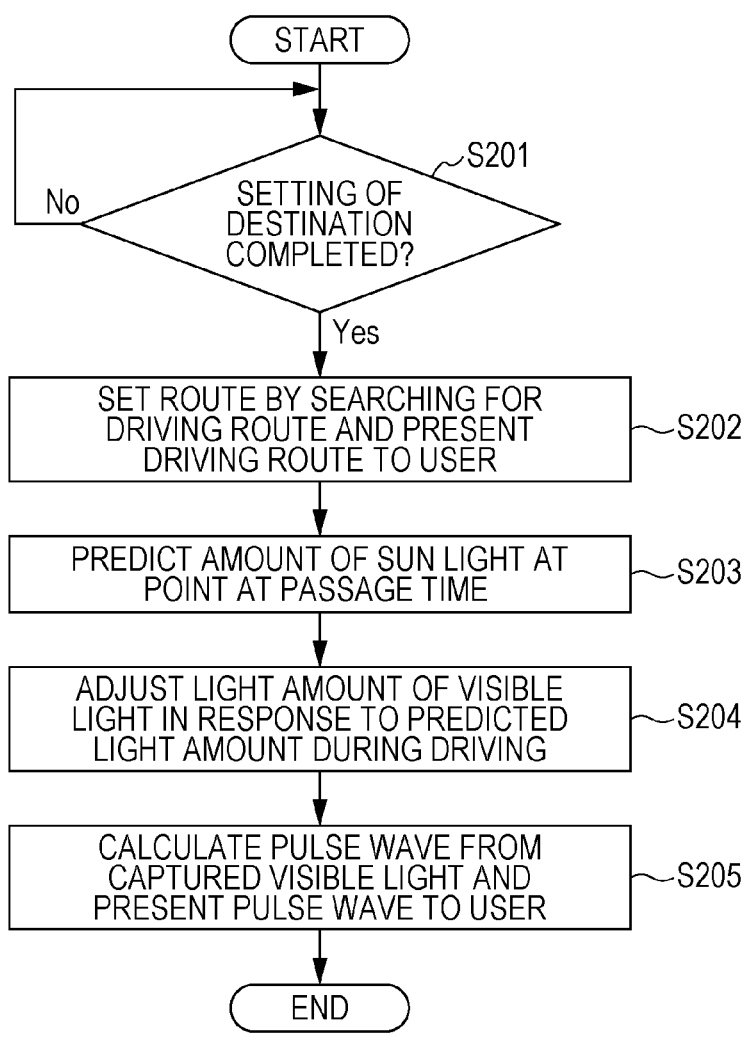
FIG. 13 is a flowchart illustrating an operation of the pulse wave measuring apparatus of the first embodiment.

FIG. 13 is a flowchart illustrating a process of the pulse wave measuring apparatus 110 of the first embodiment.

Step S201

In an interactive operation with the user 111, the route searcher 101 gives an assistance (not illustrated) to the user 111 in setting a destination point, and receives and sets the destination point input by the user 111. If the setting of the destination is complete (yes branch from step S201), processing proceeds to step S202. If the setting of the destination is not complete (no branch from step S201), step S201 is repeated. The route searcher 101 continues to assist the user 111 in setting a destination point.

Step S202

The route searcher 101 searches for an adequate guidance route, based on the destination point set in step S201, and the present position obtained from a global positioning system (GPS) (not illustrated), and sets the searched guidance route. The route is set to be used by the route setter 102 in a driving route guidance, and is displayed on the route display 103 to the user 111. The light amount predictor 108 obtains the set guidance route.

Step S203

The light amount predictor 108 predicts an amount of the sun light in the driving route of the vehicle V, based on a time of passage at each way along the guidance route searched in step S202, and the position of the sun (solar elevation angle (degrees) and solar azimuth angle (degrees)).

Step S204

Based on the amount of the sun light along the guidance route predicted by the light amount predictor 108 (predicted amount), the light source controller 109 controls the visible light emitter 107 to increase or decrease the amount of light of the visible light emitter 107 such that the sum of the predicted light amount and the amount of light of the visible light emitter 107 is a constant value (in other words, equation (1) is satisfied). The constant value may be set to be a value higher than a maximum amount of the sun light experienced from the departure point to the destination point of the guidance route set by the route setter 102 (for example, the constant value may be set to be 1.1 or 1.5 times higher than the maximum amount). If the sum is insufficient to achieve the constant value, a lacking portion of light may be compensated for by the visible light emitter 107. The amount of light illuminating the skin of the user 111 is thus kept constant.

Step S205

The visible light imager 104 receives visible light reflected from the skin of the user 111. The pulse wave calculator 105 calculates the pulse wave of the user 111 from the visible light received by the visible light imager 104.

If the incident amount of the sun light changes along the driving route from the departure point to the destination point, the pulse wave measuring apparatus 110 changes the amount of light of the visible light emitter 107 to control the variations through the series of operations described above. As a result, to obtain the pulse wave of the user 111, the visible light emitter 107 is controlled such that the amount of light illuminating the user 111 is constant. The accuracy of the obtained pulse wave is thus increased. The pulse wave measuring apparatus 110 reduces the variations in the amount of light illuminating the user 111 as a driver.

Modification of First Embodiment

With the technique of the first embodiment, the amount of light emitted from the visible light emitter 107 is controlled in accordance with the amount of the sun light entering the vehicle V at a predicted position and at a predicted time traveling along the guidance route searched for and determined by the route searcher 101. The technique is not limited to the vehicle V traveling along the guidance route, but may be applied to control the amount of light emitted from the visible light emitter 107 at the position of the vehicle V at the present time.

In this case, the light amount predictor 108 predicts how much sun light enters the vehicle V, based on position information indicating the present position of the vehicle V obtained by GPS and the present time. A specific prediction operation is performed by regarding the predictive position and the predictive time in the first embodiment as the present position and the present time.

The light source controller 109 controls the visible light emitter 107 to output an amount of light that the light amount predictor 108 calculates in accordance with the present position and the present time.

In other words, the controller of the first embodiment (D) obtains the present time and the present position of the vehicle V, and estimates the incident amount of the sun light that enters the vehicle at the present position at the present time, and (E) calculates the amount of light under a condition that a sum of the estimated incident amount and the amount is a constant value.

Through the series of operations described above, the pulse wave measuring apparatus 110 changes the amount of light of the visible light emitter 107 to control the variations in the incident amount of the sun light at the present position and the present time. To obtain the pulse wave of the user 111, the visible light emitter 107 is controlled such that the amount of light illuminating the user 111 is constant. In this way, the pulse wave measuring apparatus 110 reduces the variations in the amount of light illuminating the user 111 as a driver.

Second Embodiment

In accordance with a second embodiment, a pulse wave measuring apparatus 1702 controls the variations in the amount of light illuminating the driver in view of a weather condition. More specifically, the pulse wave measuring apparatus 1702 of the second embodiment obtains the pulse wave of the user using the sun light entering the vehicle and the light emitted from a light source in the vehicle. In accordance with the second embodiment, the light amount predictor 108 predicts the amount of light illuminating the user 111 using the sun position information 202 and weather forecast information. Elements having functionalities identical to those of the first embodiment are designated with the same reference numerals, and the discussion thereof is omitted herein.

The pulse wave measuring apparatus 1702 of the second embodiment is described below.

Figure 14:
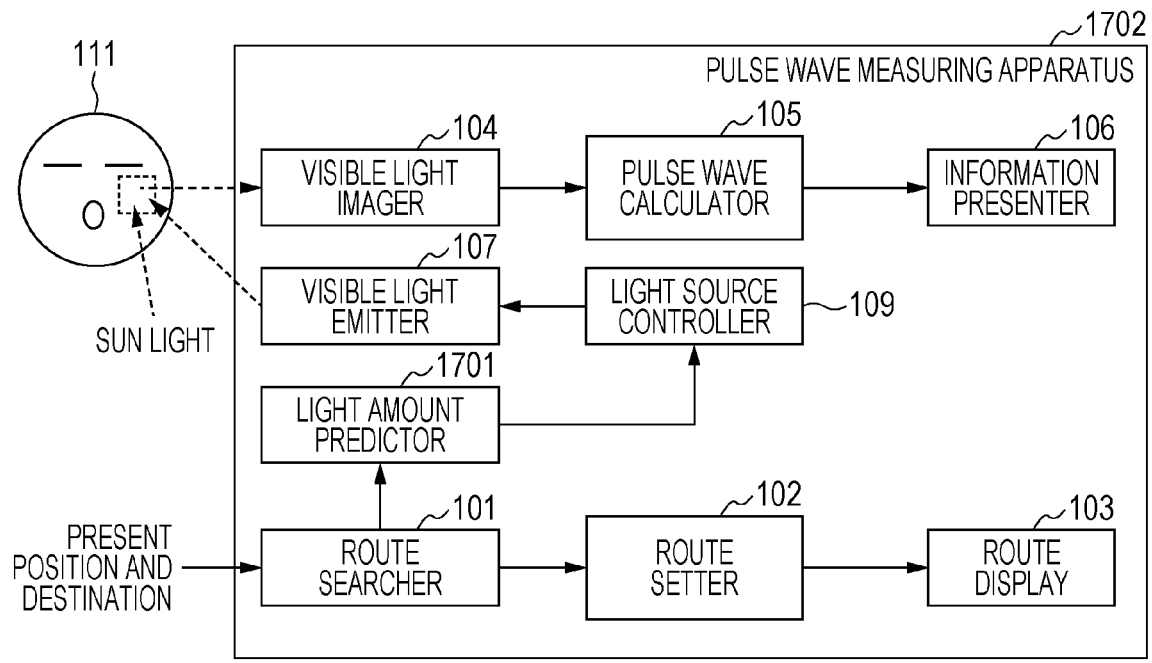
FIG. 14 is a block diagram of a pulse wave measuring apparatus of a second embodiment.
Figure 15:
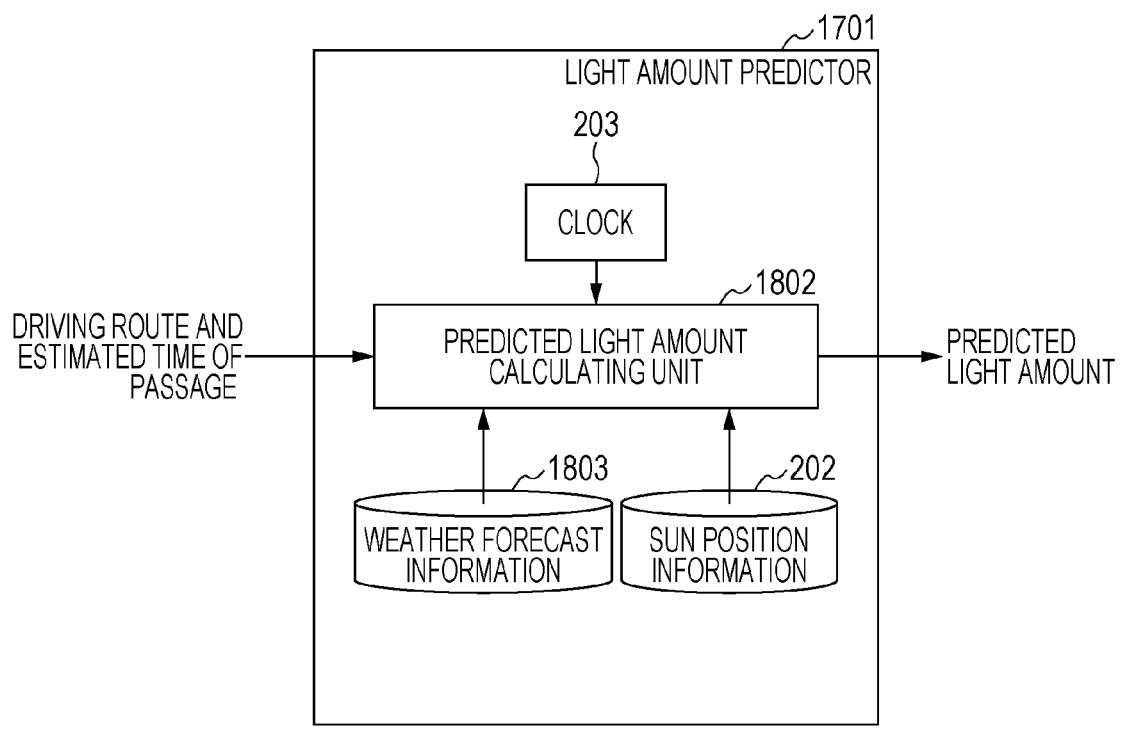
FIG. 15 is a detailed block diagram of a light amount predictor in the pulse wave measuring apparatus of the second embodiment.

FIG. 14 is a block diagram of the pulse wave measuring apparatus 1702 of the second embodiment. FIG. 15 is a detailed block diagram of a light amount predictor 1701 of the second embodiment. Referring to FIG. 15, weather forecast information 1803 is a database that stores weather information in an area where and in a time band when the vehicle V having the pulse wave measuring apparatus 1702 mounted thereon may possibly travel.

Referring to FIG. 14, the pulse wave measuring apparatus 1702 of the second embodiment includes the route searcher 101, the route setter 102, the route display 103, the visible light imager 104, the pulse wave calculator 105, the information presenter 106, the visible light emitter 107, the light amount predictor 1701, and the light source controller 109. The pulse wave measuring apparatus 1702 is different from the pulse wave measuring apparatus 110 of the first embodiment in that the pulse wave measuring apparatus 1702 includes the light amount predictor 1701.

Referring to FIG. 15, the light amount predictor 1701 includes sun position information 202, a clock 203, weather forecast information 1803, and a predicted light amount calculating unit 1802.

Light Amount Predictor

Referring to FIG. 15, the light amount predictor 1701 is different from the light amount predictor 108 in that the light amount predictor 1701 uses the weather forecast information 1803 in addition to the sun position information 202 to calculate a predicted amount of light.

In a way similar to the predicted light amount calculating unit 201 of the first embodiment, the predicted light amount calculating unit 1802 of the second embodiment predicts the direction and amount of the sun light along the guidance route.

The predicted light amount calculating unit 1802 references the weather forecast information 1803 at a time when the vehicle V passes through each point along the guidance route. The predicted light amount calculating unit 1802 corrects the predicted amount of the sun light at each point in accordance with weather at a time when the vehicle V passes through the point. If the weather is cloudy or rainy, the predicted light amount calculating unit 1802 calculates a rate of attenuation of the sun light in view of the location, thickness and type of a cloud, and corrects the predicted amount of the sun light. For example, if the weather is cloudy, the predicted light amount calculating unit 1802 may reduce the predicted amount of the sun light to half, or if the weather is rainy, the predicted light amount calculating unit 1802 may reduce the predicted amount to one-third. The predicted light amount calculating unit 1802 provides the corrected amount of the sun light as a predicted amount to the light source controller 109.

The subsequent process is identical to the process of the first embodiment, and the detailed discussion thereof is omitted herein.

The controller of the second embodiment obtains the weather information at the position of the vehicle V at the predicted time, adjusts the predicted incident amount of the sun light in accordance with the weather information, and calculates the amount of light emitted from the light emitter, based on the adjusted incident amount of the sun light.

Using the variations in the amount of the sun light depending on the weather along the driving route, the pulse wave measuring apparatus 1702 sets the amount of light illuminating the user 111 to be constant to obtain the pulse wave of the user 111. Even when the weather changes or varies, the pulse wave measuring apparatus 1702 controls the variations in the amount of light illuminating the user 111.

Third Embodiment

In accordance with a third embodiment, a pulse wave measuring apparatus 1902 controls the variations in the amount of light illuminating the driver in view of the structure of the vehicle V. More specifically, the pulse wave measuring apparatus 1902 of the third embodiment obtains the pulse wave of the user using the sun light entering the vehicle from the outside and the light emitted from a light source in the vehicle. In accordance with the third embodiment, the light amount predictor 108 predicts the amount of light illuminating the user 111 using the sun position information 202 and structure information of the vehicle V. Typically, the amount of the sun light entering the vehicle V varies depending on the color or shape of the hood of the vehicle V. The amount of light illuminating the user 111 are controlled even more using the structure information of the vehicle V. Elements having functionalities identical to those of the first embodiment are designated with the same reference numerals, and the detailed discussion thereof is omitted herein.

The pulse wave measuring apparatus 1902 of the third embodiment is described below.

Figure 16:
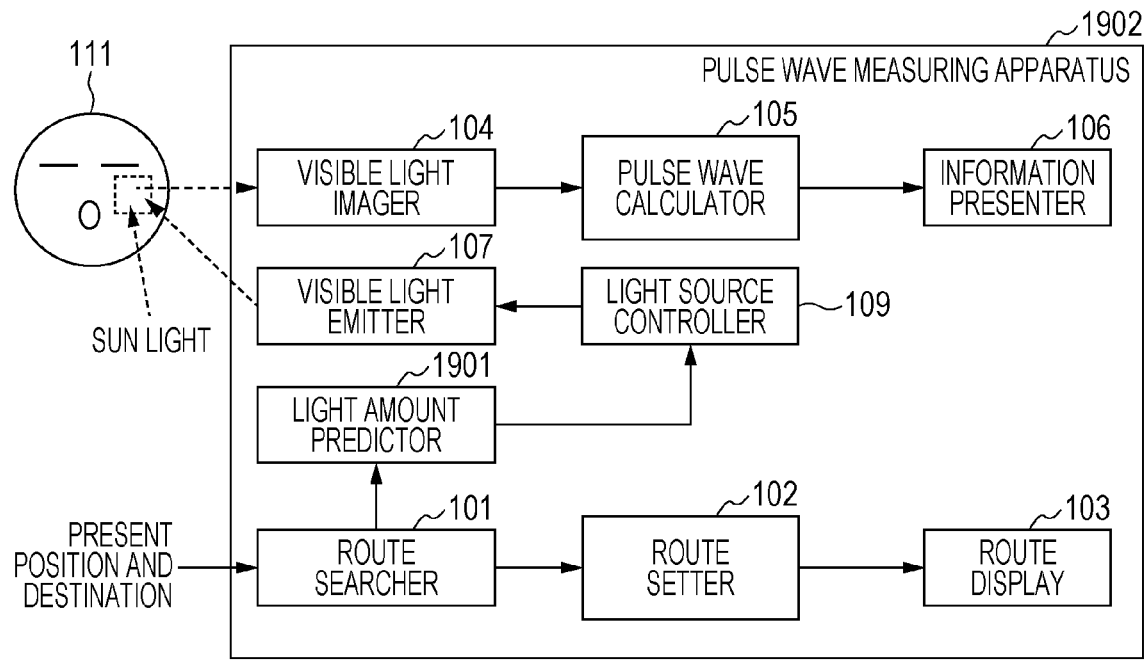
FIG. 16 is a block diagram of a pulse wave measuring apparatus of a third embodiment.
Figure 17:
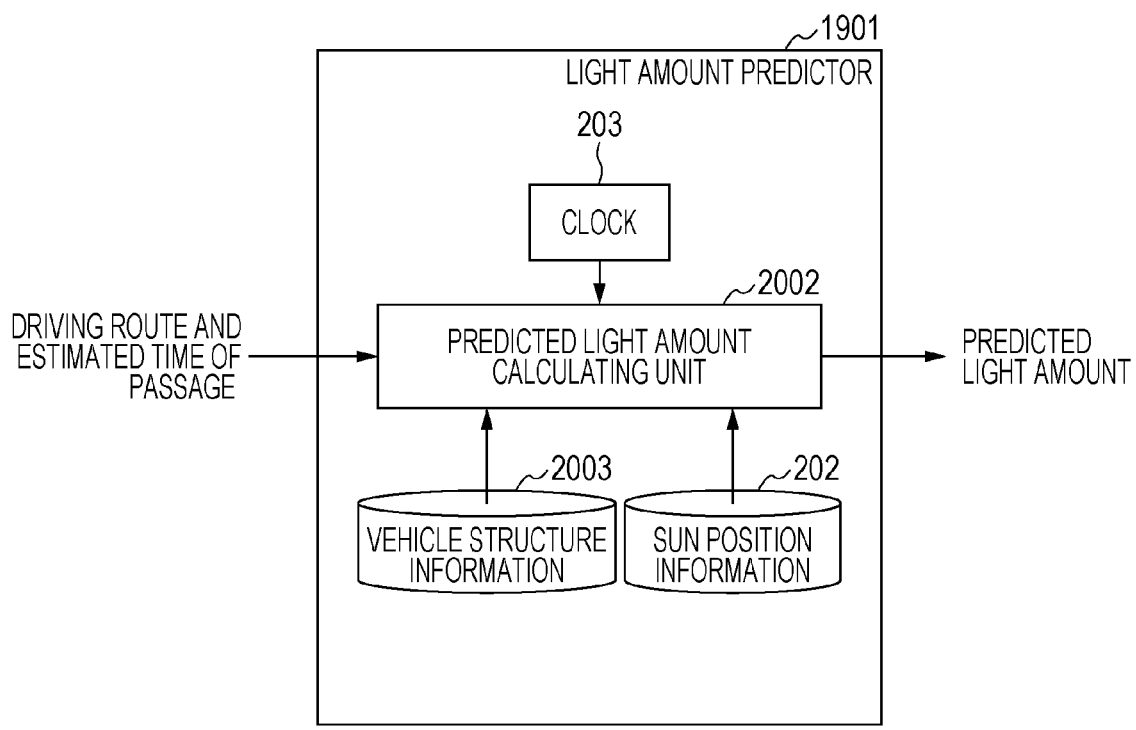
FIG. 17 is a detailed block diagram of a light amount predictor in the pulse wave measuring apparatus of the third embodiment.

FIG. 16 is a block diagram of the pulse wave measuring apparatus 1902 of the third embodiment. FIG. 17 is a detailed block diagram of a light amount predictor 1901 of the third embodiment.

Referring to FIG. 16, the pulse wave measuring apparatus 1902 of the third embodiment includes the route searcher 101, the route setter 102, the route display 103, the visible light imager 104, the pulse wave calculator 105, the information presenter 106, the visible light emitter 107, the light amount predictor 1901, and the light source controller 109.

The pulse wave measuring apparatus 1902 is different from the pulse wave measuring apparatus 110 of the first embodiment in that the pulse wave measuring apparatus 1902 includes the light amount predictor 1901.

Referring to FIG. 17, the light amount predictor 1901 includes vehicle structure information 2003, a clock 203, sun position information 202, and a predicted light amount predicting unit 2002.

Light Amount Predictor

Referring to FIG. 17, the light amount predictor 1901 is different from the light amount predictor 108 of the first embodiment in that the light amount predictor 1901 uses the vehicle structure information 2003 in addition to the sun position information 202 to calculate a predicted amount of light.

In a way similar to the predicted light amount calculating unit 201 of the first embodiment, the predicted light amount calculating unit 2002 of the third embodiment predicts the direction and amount of the sun light along the guidance route using the sun position information 202.

The predicted light amount calculating unit 2002 references the vehicle structure information 2003 of the vehicle V, and corrects the predicted amount of the sun light in view of a factor of the structure of the vehicle V that may increase or decrease the amount of the sun light illuminating the user 111 as a driver. For example, using the vehicle structure information 2003 of the vehicle V, the predicted light amount calculating unit 2002 corrects the predicted amount of the sun light.

Figures 18, 19:
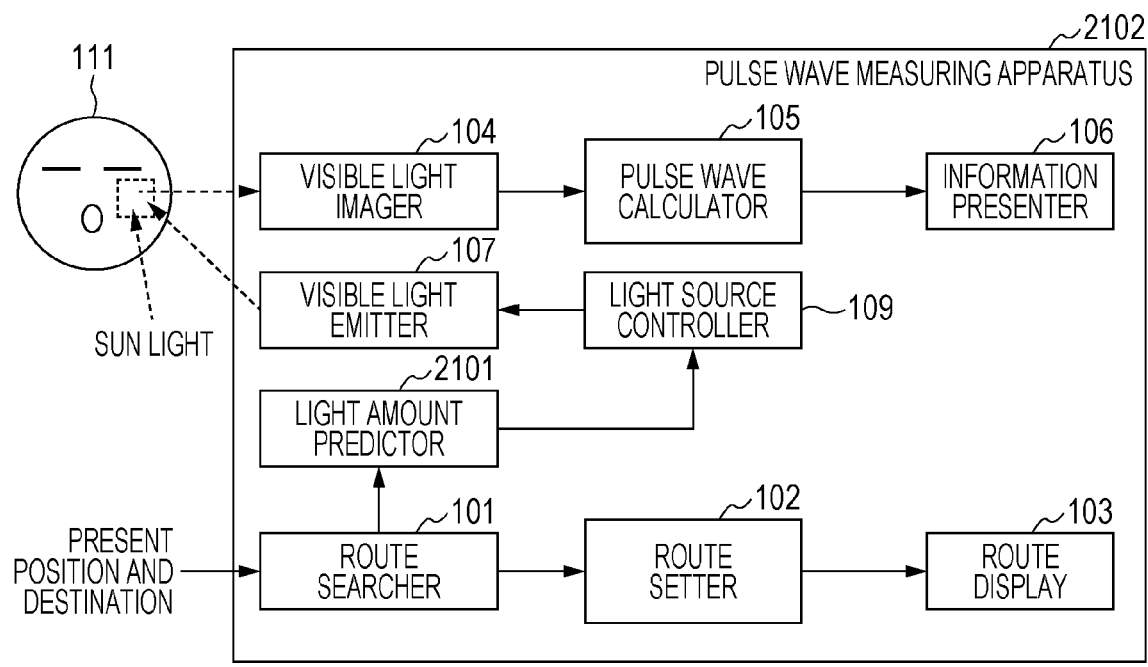
FIG. 18 illustrates structure information of the vehicle in accordance with the third embodiment.
FIG. 19 is a block diagram of a pulse wave measuring apparatus of a fourth embodiment.

FIG. 18 illustrates the vehicle structure information 2003 of the vehicle V in accordance with the third embodiment.

Referring to FIG. 18, the vehicle structure information 2003 of the vehicle V is a database that associates factors increasing or decreasing the amount of the sun light illuminating the user 111, out of information indicative of the vehicle structure, with an amount of increase or decrease (such as a magnification) of the amount of the sun light responsive to the factors. The factors includes the color, material, or shape of the dashboard of the vehicle V, or the color or shape of the hood of the vehicle V, the presence or absence of the roof of the vehicle V, or the type or shape of the windshield or side window glass.

If the vehicle structure information 2003 indicates that the predicted light amount calculating unit 2002 multiplies the amount of the sun light by 1.2 for correction if the color of the dashboard of the vehicle V is white, for example. If the vehicle V has no roof provided, the vehicle structure information 2003 indicates that the predicted light amount calculating unit 2002 multiplies the amount of the sun light by 2.

In this way, the predicted light amount calculating unit 2002 corrects the amount of the sun light by multiplying the predicted amount of the sun light by a magnification associated with the factor of the corresponding vehicle V included in the vehicle structure information 2003 of the vehicle V. The predicted light amount calculating unit 2002 sends the corrected amount of the sun light as a predicted amount to the light source controller 109.

The subsequent process is identical to the process of the first embodiment, and the detailed discussion thereof is omitted herein.

The controller of the third embodiment obtains the vehicle structure information 2003 of the vehicle V, adjusts the predicted amount of the sun light in accordance with the structure information, and calculates the amount of the sun light using the adjusted incident amount of the sun light.

In view of the vehicle structure information 2003 of the vehicle V, the pulse wave measuring apparatus 1902 sets the amount of light illuminating the user 111 to be constant to obtain the pulse wave of the user 111. Even when the vehicle structure information 2003 of the vehicle V changes or varies, the pulse wave measuring apparatus 1902 controls the variations in the amount of light illuminating the user 111.

Fourth Embodiment

In accordance with a fourth embodiment, a pulse wave measuring apparatus 2102 controls the variations in the amount of light illuminating the driver in view of building information concerning buildings surrounding the route. More specifically, the pulse wave measuring apparatus 2102 of the fourth embodiment obtains the pulse wave of the user using the sun light entering the vehicle from the outside and the light emitted from a light source in the vehicle. In accordance with the third embodiment, the light amount predictor 108 predicts the amount of light illuminating the user 111 using the building information surrounding the driving route in addition to the sun position information 202. Elements having functionalities identical to those of the first embodiment are designated with the same reference numerals, and the discussion thereof is omitted herein.

The pulse wave measuring apparatus 2102 of the fourth embodiment is described below.

Figure 20:
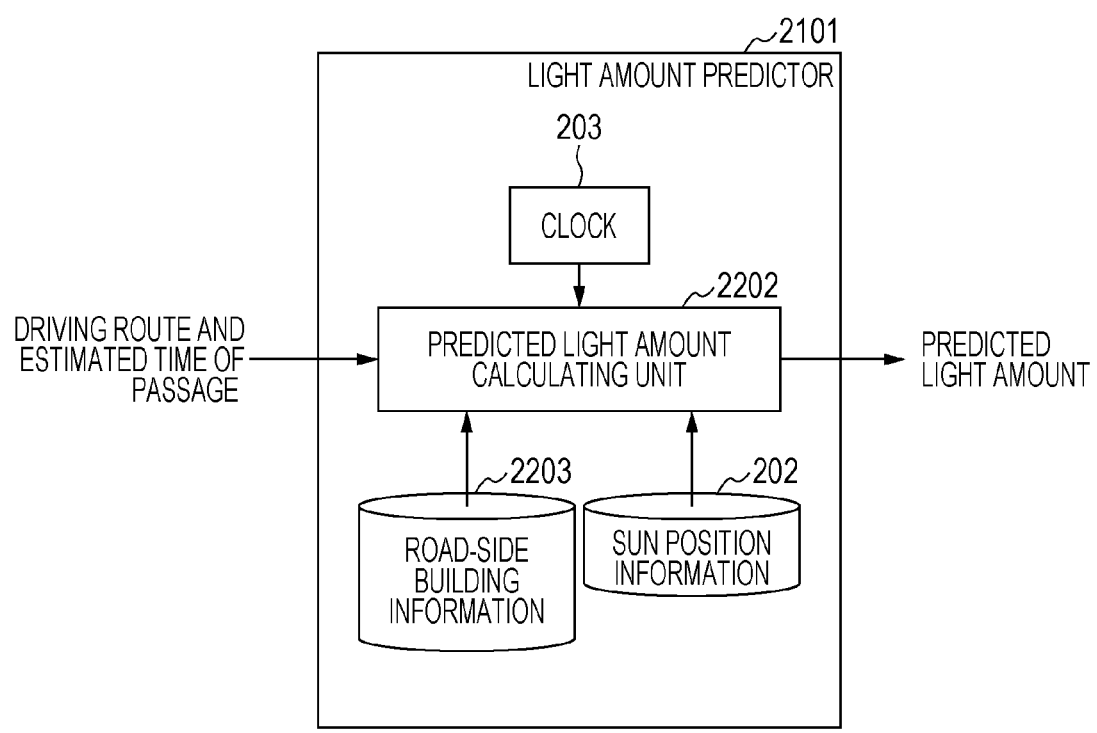
FIG. 20 is a detailed block diagram of a light amount predictor in the pulse wave measuring apparatus of the fourth embodiment.

FIG. 19 is a block diagram of the pulse wave measuring apparatus 2102 of the fourth embodiment and FIG. 20 is a detailed block diagram of a light amount predictor 2101 of the fourth embodiment. Road-side building information 2203 is related to buildings, walls, or tunnels surrounding the guidance road and serves as a factor that increases or decreases the amount of the sun light illuminating the user 111 as a driver.

Referring to FIG. 19, the pulse wave measuring apparatus 2102 of the fourth embodiment includes the route searcher 101, the route setter 102, the route display 103, the visible light imager 104, the pulse wave calculator 105, the information presenter 106, the visible light emitter 107, the light amount predictor 2101, and the light source controller 109. The pulse wave measuring apparatus 2102 is different from the pulse wave measuring apparatus 110 of the first embodiment in that the pulse wave measuring apparatus 2102 includes the light amount predictor 2101.

Referring to FIG. 20, the light amount predictor 2101 includes road-side building information 2203, a clock 203, sun position information 202, and a predicted light amount calculating unit 2202.

Light Amount Predictor

As illustrated in FIG. 20, the light amount predictor 2101 is different from the light amount predictor 108 of the first embodiment in that the light amount predictor 2101 uses the road-side building information 2203 concerning the buildings surrounding the route in addition to the sun position information 202 to calculate the predicted amount of light.

In a way similar to the predicted light amount calculating unit 201 of the first embodiment, the predicted light amount calculating unit 2202 of the fourth embodiment predicts the direction and amount of the sun light along the guidance route using the sun position information 202.

The predicted light amount calculating unit 2202 corrects the amount of the sun light using the road-side building information 2203 concerning the buildings surrounding the route. The road-side building information 2203 concerning the buildings surrounding the route is described with reference to FIG. 21 and FIG. 22. The buildings surrounding the route may serve as a factor that increases or decreases the amount of the sun light illuminating the user 111.

Figure 21:
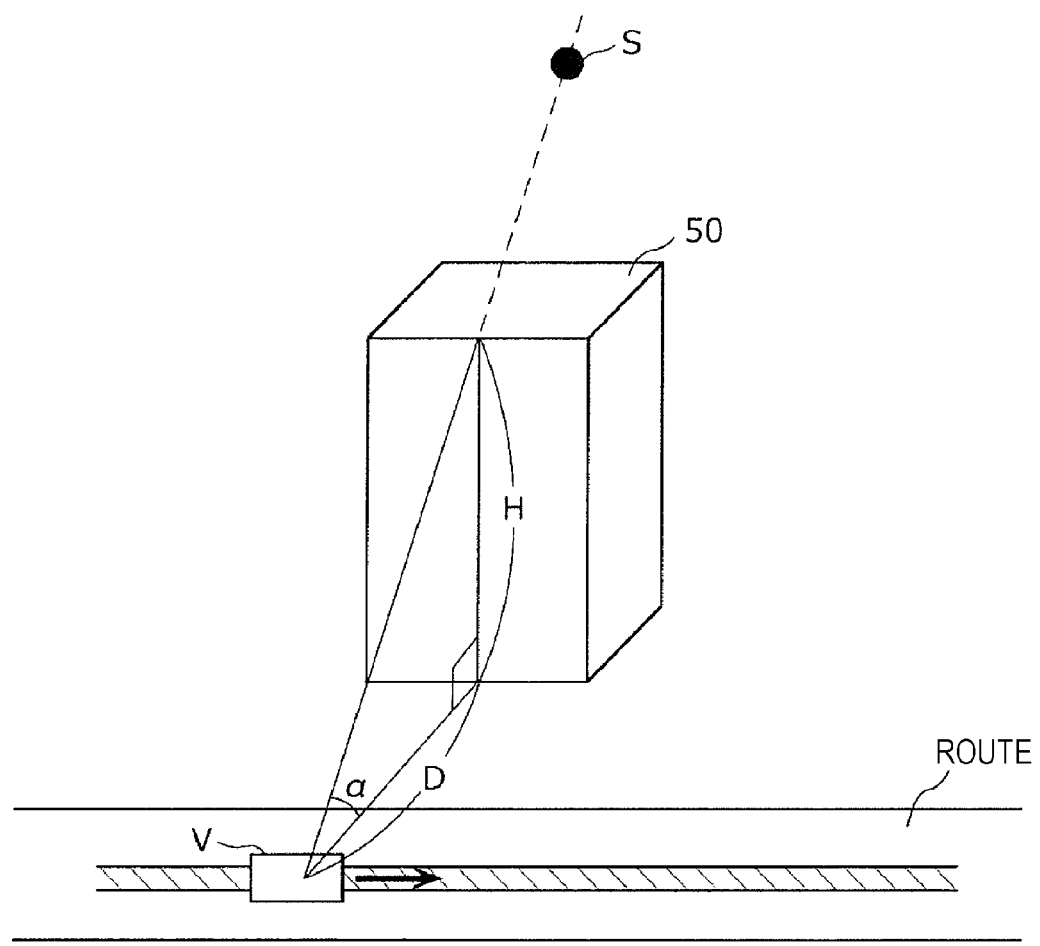
FIG. 21 illustrates a maximum value of a sun elevation angle at which a route is overshadowed in accordance with the fourth embodiment.
Figure 22:
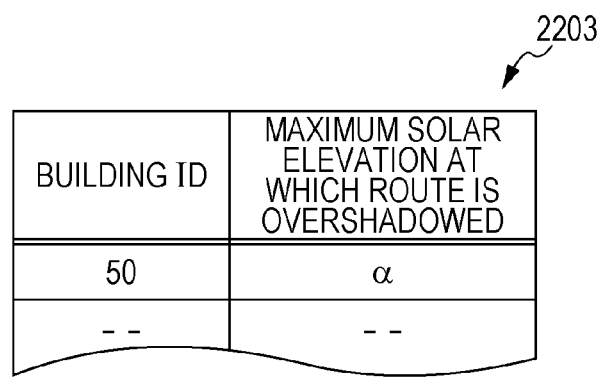
FIG. 22 illustrates building information of buildings around a route in accordance with the fourth embodiment.

FIG. 21 illustrates a maximum value of a sun elevation angle at which a route is overshadowed in accordance with the fourth embodiment. FIG. 22 illustrates building information of buildings around the route in accordance with the fourth embodiment;

Referring to FIG. 21, a building 50 having a height of H is now located at a distance of D away from the route. The sun light illuminates the vehicle V if the elevation angle of the sun S is $\alpha$ or higher. If the elevation angle of the sun S is lower than $\alpha$, the sun light is blocked by the building 50, and the sun light does not illuminate the vehicle V. The vehicle V is thus in the shadow of the building 50. Here, $\alpha$ is calculated in accordance with equation (2):

$$\alpha = \tan^{-1}(H/D) \qquad (2)$$

The road-side building information 2203 of the nearby buildings is a database that associates the building 50 that is located near the guidance route with a maximum value of the elevation angle at which the guidance route is in the shadow of the building 50. The road-side building information 2203 associates a calculated in accordance with equation (2) with the building 50. The distance of D and the height of H to calculate $\alpha$ are obtained from map information disclosed to public. The road-side building information 2203 of the nearby buildings is used to determine whether the light path of the sun light illuminating the route is blocked by the building.

The predicted light amount calculating unit 2202 references the road-side building information 2203 of the nearby buildings, and corrects the predicted amount of the sun light depending on whether the light path of the sun light illuminating the vehicle V is blocked by the building 50. More specifically, the predicted light amount calculating unit 2202 corrects the predicted amount of the sun light to a specific value if the elevation angle of the sun is lower than the "maximum value of the elevation angle at which the guidance route is in the shadow of the building 50". The specific value does not accounts for a contribution by the direction sun light but includes a contribution by scattered light of the sun light.

Another example of the road-side building information 2203 related to the nearby buildings is a tunnel. No sun light illuminates the vehicle V while the vehicle V is passing through the tunnel. For this reason, the predicted light amount calculating unit 2202 corrects the calculated amount of the sun light to a specific amount of light, namely, an amount of light emitted by lights inside the tunnel.

The predicted light amount calculating unit 2202 sends the corrected amount of the sun light (the predicted amount of the sun light if not modified) as a predicted amount of light to the light source controller 109.

The subsequent process is identical to the process of the first embodiment, and the detailed discussion thereof is omitted herein.

The controller of the fourth embodiment obtains the building information of the buildings surrounding the driving route of the vehicle V, adjusts the predicted amount of the sun light in accordance with the building information, and calculates the amount of light emitted from the light emitter using the adjusted incident amount of the sun light.

In view of the building information of the buildings surrounding the driving route, the pulse wave measuring apparatus 1902 sets the amount of light illuminating the user 111 to be constant to obtain the pulse wave of the user 111.

Even when the buildings surrounding the driving route of the vehicle V changes or varies, the pulse wave measuring apparatus 1902 controls the variations in the amount of light illuminating the user 111.

Fifth Embodiment

In accordance with a fifth embodiment, a pulse wave measuring apparatus 2303 controls the variations in the amount of light illuminating the driver by selecting from multiple route candidates a route that has a smaller variation in the amount of light illuminating the driver.

The pulse wave measuring apparatus 2303 is described below. Elements having functionalities identical to those of the first embodiment are designated with the same reference numerals, and the discussion thereof is omitted herein.

Figure 23:
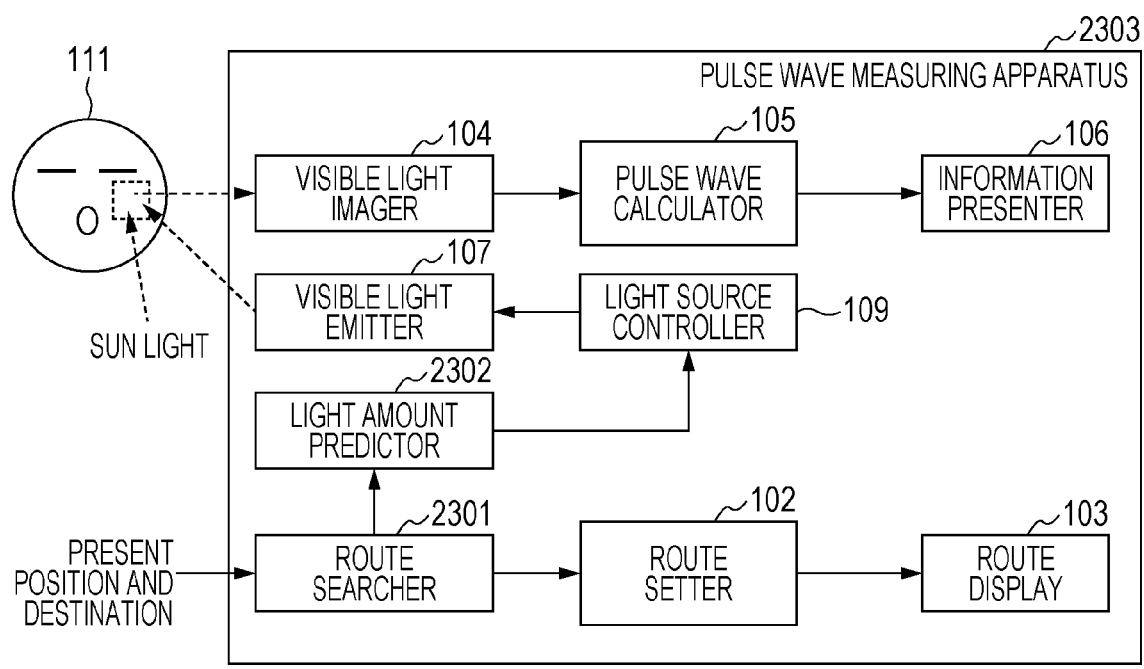
FIG. 23 is a block diagram of a pulse wave measuring apparatus in accordance with a fifth embodiment.

FIG. 23 is a block diagram of the pulse wave measuring apparatus 2303 in accordance with the fifth embodiment.

Referring to FIG. 23, the pulse wave measuring apparatus 2303 of the fifth embodiment includes a route searcher 2301, the route setter 102, the route display 103, the visible light imager 104, the pulse wave calculator 105, the information presenter 106, the visible light emitter 107, a light amount predictor 2302, and the light source controller 109.

The pulse wave measuring apparatus 2303 of the fifth embodiment selects with a higher priority as the driving route one of routes having a smaller variation in the amount of the sun light illuminating the user 111. In other words, the pulse wave measuring apparatus 2303 searches for the driving route having a smaller variation in the amount of the sun light illuminating the user 111. In this way, the variations in the amount of visible light are reduced, and the calculation accuracy of the pulse wave is increased.

Route Searcher

The route searcher 2301 searches for multiple guidance route candidates of the vehicle V in accordance with the obtained present position and destination point.

Light Amount Predictor

The light amount predictor 2302 calculates a predicted amount of light along each of the guidance routes searched for by the route searcher 2301, searches for one of the route candidates having the smallest variation in the amount of light, and notifies the route searcher 2301 of the searched route. The phrase "the smaller variation in the amount of light" means that the absolute value of the variation in the amount of light of the light source is smaller, and even if the amount of light varies slowly in a smaller range, this falls within the scope of "the smaller variation in the amount of light". The amount of light that varies slowly is easy to set to a constant value.

Figure 24A:
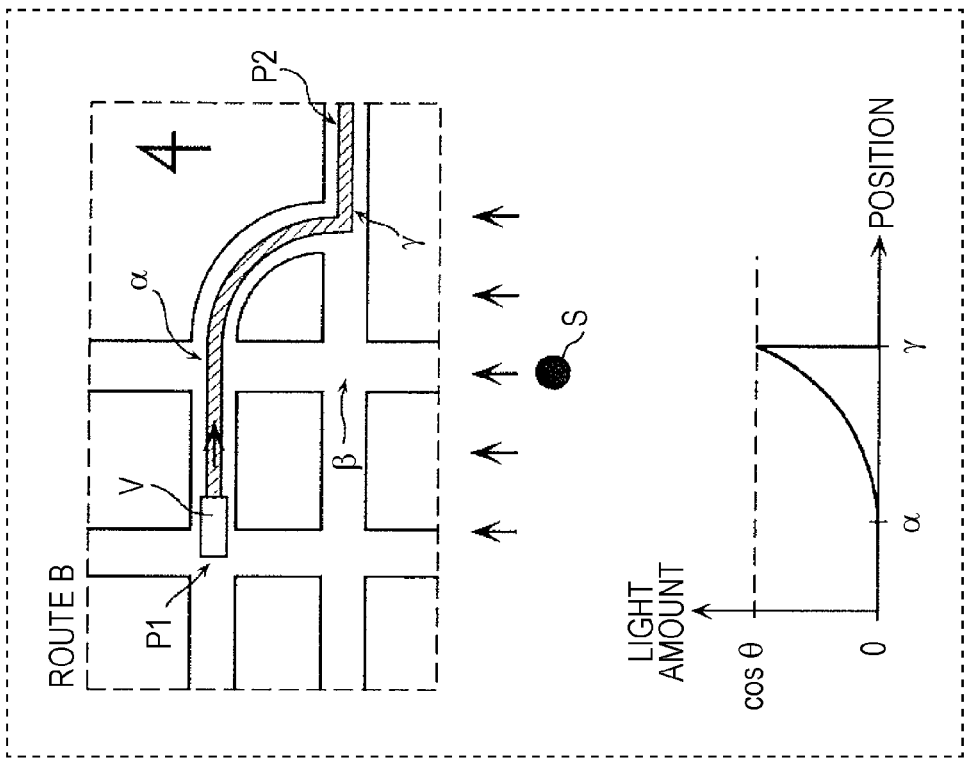
FIG. 24A and FIG. 24B illustrate an example of a route search method in accordance with the fifth embodiment.
Figure 24B:
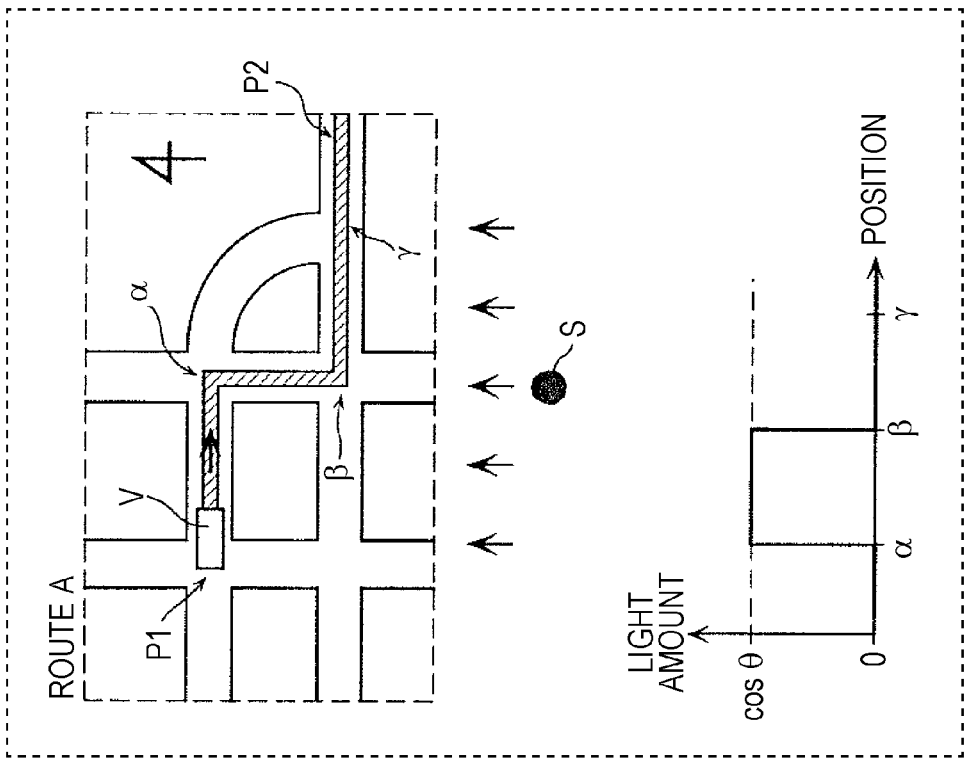

FIG. 24A and FIG. 24B illustrate an example of a route search method in accordance with the fifth embodiment. Referring to FIG. 24A and FIG. 24B, the route searcher 2301 and the light amount predictor 2302 search for the driving route having a smaller variation in the amount of light. The upper portion of each of FIG. 24A and FIG. 24B indicates the route along which the vehicle V travels, and the sun light illuminates the vehicle V from the south (from the right hand side of the page). The lower portion of each of FIG. 24A and FIG. 24B indicates variations in the amount of the sun light entering the vehicle V that travels along each route.

The vehicle V is traveling from point P1 to point P2. There are two routes, namely, a route A and a route B, from point P1 to point P2. Along the route A as illustrated in FIG. 24A, the vehicle V travels straight, and takes a right turn at an intersection α, a left turn at an intersection β, and travels straight at an intersection γ. Along the route B as illustrated in FIG. 24B, the vehicle V travels straight the intersection α, travels along a curve and then takes a left turn at the intersection γ. How the user 111 is illuminated with the sun light is considered when the vehicle V travels along each route.

The amount of the sun light is expressed by $\cos\theta \times \cos\phi$ as illustrated in FIG. 8B, wherein let $\phi$ represent the illuminating angle of the sun light and $\theta$ represent the elevation angle of the sun, each angle with respect to the advance direction. If the advance direction is changed when the vehicle V takes a right or left turn at an intersection, the angle $\phi$ varies. The variation in the angle $\phi$ is determined by an amount of angle in the advance direction and the illuminating angle $\phi$ of the sun light.

For example, the vehicle V may now travel along the route A. When the vehicle V takes a right turn at the intersection α, the illuminating angle $\phi$ of the sun light sharply changes from $-\pi/2$ to 0. Along with this change, the amount of the sun light sharply changes from 0 to $\cos\theta$. Similarly, when the vehicle V takes a left turn at the intersection β, the amount of the sun light sharply changes from $\cos\theta$ to 0 (see the lower portion of FIG. 24A).

In contrast, the vehicle V may travel along the route B. The illuminating angle $\phi$ of the sun light slowly changes from $-90/2$ to 0 when the vehicle V travels along the curved route from the intersection α to the intersection γ. Along with the driving, the amount of the sun light slowly changes from 0 to $\cos\theta$. When the vehicle V takes a left turn at the intersection γ, the amount of the sun light sharply changes from $\cos\theta$ to 0 (see the lower portion of FIG. 24B).

In comparison of the two routes of FIG. 24A and FIG. 24B, the route B has a smaller variation in the amount of the sun light entering the vehicle V. Along the route A, the vehicle V takes two turns, the left turn and the right turn. Along the route B, in contrast, the vehicle V takes a single turn, namely, the left turn.

From the above discussion, the route B is determined to have a smaller variation in the amount of the sun light entering the vehicle V. The light amount predictor 2302 selects the route B as a route having a smaller variation in the amount of light, and notifies the route searcher 2301 of the route B.

FIG. 25 is a flowchart illustrating an operation of the pulse wave measuring apparatus 2303 of the fifth embodiment.

Step S2501

In an interactive operation with the user 111 as a driver or a fellow passenger, the route searcher 2301 gives an assistance (not illustrated) to the user 111 in setting a destination point, receives the destination point input by the user 111, and sets the destination point. If the setting of the destination is complete (yes branch from step S2501), processing proceeds to step S2502. If the setting of the destination is not complete (no branch from step S2501), step S2501 is repeated. The route searcher 2301 continues to assist the user 111 in setting a destination point.

Step S2502

The route searcher 2301 searches for multiple guidance route candidates, based on the destination point set in step S2501, and the present position obtained from a GPS receiver (not illustrated), and outputs the multiple guidance route candidates. For example, as described above, the route that runs along a naturally curved line has a smaller variation in the amount of the sun light entering the vehicle V than a route that have a right turn and left turn. With this knowledge, even if a route searched for has left and right turns at intersections, route searching may be continued to search for a route that has a naturally curved line.

Step S2503

The light amount predictor 2302 predicts the amount of the sun light along each of the guidance route candidates of the vehicle V searched for in step S2502, based on the time of passage, and the position of the sun (the solar elevation angle (degrees), and the solar azimuth angle (degrees)) at each point along each guidance route candidate.

Step S2504

The light amount predictor 2302 selects and sets as the guidance route one of the guidance route candidates searched for in step S2503 having the smallest variation in the amount of the sun light entering the vehicle V.

Step S2505

Based on the amount of the sun light along the guidance route predicted by the light amount predictor 2302 (predicted light amount), the light source controller 109 controls the visible light emitter 107 such that the amount of light of the visible light emitter 107 increases or decreases along the guidance route of the vehicle V. The method of control is identical to the operation in step S204 of the first embodiment and the discussion thereof is omitted herein.

Step S2506

The visible light imager 104 receives visible light reflected from the skin of the user 111. The pulse wave calculator 105 calculates the pulse wave of the user 111 from the visible light received by the visible light imager 104.

The controller of the fifth embodiment obtains the multiple driving route candidates from the present position to the destination point of the vehicle, obtains the estimated time of passage at a location along each of the obtained driving route candidates, predicts the incident amount of the sun light entering the vehicle at the location at the time of passage, and obtains as a driving route with a higher priority one of the route candidates having a smaller variation in the incident amount of the sun light predicted along the driving route candidate.

In this way, the pulse wave measuring apparatus 2303 uses as the driving route one of the driving route candidates having a relatively smaller variation in the incident amount of the sun light. The vehicle thus travels along the route having the relatively smaller variation in the incident amount of the sun light, and the variation in the sun light illuminating the user 111 during driving is controlled. As a result, the pulse wave measuring apparatus 2303 even more controls the variations in the amount of light illuminating the user 111 as a driver.

Modifications of Embodiments

Elements of the pulse wave measuring apparatuses of the embodiments are described below.

FIG. 26 is a block diagram of a pulse wave measuring apparatus 110A of a modification.

Referring to FIG. 26, the pulse wave measuring apparatus 110A includes an imager 104A, a pulse wave calculator 105A, a light emitter 107A, and a controller 109A.

The light emitter 107A illuminates with light an area including at least the skin of the user 111 staying in the vehicle V.

The imager 104A obtains an image of the area including the skin of the user 111.

The controller 109A (A) obtains a driving route from a departure point to a destination point of a vehicle, (B) obtains an estimated time of passage of the vehicle that passes through a location along the driving route, and predicts an incident amount of sun light that enters the vehicle at the location at the estimated time of passage, and (C) controls an amount of light of the light emitter 107A at the location by calculating the amount of light of the light emitter 107A such that a sum of the predicted incident amount of the sun light and the amount of light of the light emitter 107A is a constant value.

The pulse wave calculator 105A calculates the pulse wave of the user 111 using the image, and outputs pulse wave information of the user 111.

The pulse wave measuring apparatus thus controls the variations in the amount of light illuminating the driver.

In accordance with the embodiments 110A, each element may be implemented using dedicated hardware, or may be implemented by executing a software program for each element. Each element may be implemented by a program executing unit, such as a CPU or a processor, which reads the software program stored on a recording medium, such as a hard disk or a semiconductor device and executes the read software program. The software program that implements the pulse wave measuring apparatuses of the embodiments is described below.

The software program causes a computer to perform a control process of the pulse wave measuring apparatus. The pulse wave measuring apparatus includes a light emitter that emits light having an amount to an area containing at least part of skin of a user staying in a vehicle, and an imager that captures an image of the area. The control process includes (A) obtaining a driving route from a departure point of the vehicle to a destination point of the vehicle, (B) obtaining an estimated time at which the vehicle passes through a location along the driving route, and predicting an incident amount of sun light that enters the vehicle at the location at the estimated time, and (C) calculates the amount under a condition that a sum of the predicted incident amount and the amount is a constant value, calculating a pulse wave of the user using the image, and outputting pulse wave information of the user.

The software program causes a computer to perform a control process of the pulse wave measuring apparatus. The pulse wave measuring apparatus includes a light emitter that emits light having an amount to an area containing at least part of skin of a user staying in a vehicle, and an imager that captures an image of the area. The control process includes (D) obtaining a present time and a present position of a vehicle, and estimating an incident amount of sun light that enters the vehicle at the present position at the present time, and (E) calculates the amount under a condition that a sum of the incident amount of the sun light and the amount is a constant value, calculating a pulse wave of the user using the image, and outputting pulse wave information of the user.

Each of the pulse wave measuring apparatuses of the disclosure is constructed as described above. The user as a driver may accurately detect the pulse wave of the user during driving. The pulse wave measuring apparatus may monitor the health condition of the driver on a real-time basis. If any irregularity occurs, the driving may be suspended. During the driving that may make the driver tense, the pulse wave of the driver is recorded every moment, and is compared with the pulse wave of the driver at rest.

What is claimed is:

1. A pulse wave measuring apparatus, comprising:
a light emitter that illuminates with light having an amount an area containing a part of skin of a user staying in a vehicle;
an imager that captures an image of the area;
a controller that
(A) obtains a driving route from a departure point of the vehicle to a destination point of the vehicle,
(B) obtains an estimated time at which the vehicle passes through a location along the driving route, and predicts an incident amount of sun light that enters the vehicle at the location at the estimated time, and (C) calculates the amount under a condition that a sum of the predicted incident amount and the amount is a constant value; and a pulse wave calculator that calculates a pulse wave of the user using the image, and outputs pulse wave information of the user, wherein the controller, when obtaining the driving route, obtains driving route candidates from the departure point to the destination point, obtains a candidate estimated time at which the vehicle passes through a candidate location along each of the obtained driving route candidates, predicts a candidate incident amount of sun light entering the vehicle at the candidate location at the candidate estimated time, and obtains, as the driving route with a higher priority, a driving route candidate having a smaller variation in the predicted candidate incident amount from among the driving route candidates.

2. The pulse wave measuring apparatus according to claim 1, wherein the controller obtains weather information at the location at the estimated time, adjusts the predicted incident amount in accordance with the weather information, and calculates the amount using the adjusted incident amount.

3. The pulse wave measuring apparatus according to claim 1, wherein the controller obtains structure information of the vehicle, adjusts the predicted incident amount in accordance with the structure information, and calculates the amount using the adjusted incident amount.

4. The pulse wave measuring apparatus according to claim 1, wherein the controller obtains building information of buildings around the location, adjusts the predicted incident amount in accordance with the building information, and calculates the amount using the adjusted incident amount.

5. A pulse wave measuring apparatus, comprising:
a light emitter that illuminates with light having an amount an area containing a part of skin of a user staying in a vehicle;
an imager that captures an image of the area;
a controller that
(D) obtains a present time and a present position of the vehicle, and estimates an incident amount of sun light that enters the vehicle at the present position at the present time, and
(E) calculates the amount under a condition that a sum of the estimated incident amount and the amount is a constant value; and
a pulse wave calculator that calculates a pulse wave of the user using the image, and outputs pulse wave information of the user.

6. A control method, comprising:
obtaining a driving route from a departure point of a vehicle to a destination point of the vehicle;
obtaining an estimated time at which the vehicle passes through a location along the driving route;
predicting an incident amount of sun light entering the vehicle at the location at the estimated time;
calculating an amount of light emitted from a light emitter under a condition that a sum of the incident amount and the amount is a constant value;
causing the light emitter at the location to emit light at the amount to illuminate an area containing skin of a user staying in the vehicle;
obtaining an image containing an image of the skin;
calculating a pulse wave of the user using the image; and
outputting information related to the pulse wave.

7. A control method, comprising:
obtaining a present time and a present position of a vehicle;
estimating an incident amount of sun light entering the vehicle at the present position at the present time;
calculating an amount of light emitted from a light emitter under a condition that a sum of the incident amount and the amount is a constant value;
causing the light emitter to emit light at the amount to illuminate an area containing skin of a user staying in the vehicle;
obtaining an image containing an image of the skin;
calculating a pulse wave of the user using the image; and
outputting information related to the pulse wave.

8. A non-transitory computer-readable recording medium being non-volatile and storing a control program causing an apparatus including a processor to perform a process, the process comprising:
obtaining a driving route from a departure point of a vehicle to a destination point of the vehicle;
obtaining an estimated time at which the vehicle passes through a location along the driving route;
predicting an incident amount of sun light entering the vehicle at the location at the estimated time;
calculating an amount of light emitted from a light emitter under a condition that a sum of the incident amount and the amount is a constant value;
causing the light emitter at the location to emit light at the amount to illuminate an area containing skin of a user staying in the vehicle;
obtaining an image containing an image of the skin;
calculating a pulse wave of the user using the image; and
outputting information related to the pulse wave.

9. A non-transitory computer-readable recording medium being non-volatile and storing a control program causing an apparatus including a processor to perform a process, the process comprising:
obtaining a present time and a present position of a vehicle;
estimating an incident amount of sun light entering the vehicle at the present position at the present time;
calculating an amount of light emitted from a light emitter under a condition that a sum of the incident amount and the amount is a constant value;
causing the light emitter to emit light at the amount to illuminate an area containing skin of a user staying in the vehicle;
obtaining an image containing an image of the skin;
calculating a pulse wave of the user using the image; and
outputting information related to the pulse wave.

* * * * *